United States Patent
Balczewski et al.

(10) Patent No.: US 11,179,106 B2
(45) Date of Patent: Nov. 23, 2021

(54) WEARABLE DEVICE TO DISPOSABLE PATCH CONNECTION VIA CONDUCTIVE ADHESIVE

(71) Applicant: Cardiac Pacemakers, Inc., St. Paul, MN (US)

(72) Inventors: Ron A. Balczewski, Bloomington, MN (US); Aleksandra Kharam, Maple Grove, MN (US)

(73) Assignee: Cardiac Pacemakers, Inc., St Paul (MN)

( * ) Notice: Subject to any disclaimer, the term of this patent is extended or adjusted under 35 U.S.C. 154(b) by 145 days.

(21) Appl. No.: 16/355,009

(22) Filed: Mar. 15, 2019

(65) Prior Publication Data

US 2019/0282167 A1    Sep. 19, 2019

Related U.S. Application Data

(60) Provisional application No. 62/644,272, filed on Mar. 16, 2018.

(51) Int. Cl.
*A61B 5/00* (2006.01)
*A61B 5/0408* (2006.01)
(Continued)

(52) U.S. Cl.
CPC ............ *A61B 5/6833* (2013.01); *A61B 5/259* (2021.01); *A61B 5/282* (2021.01); *A61B 5/0024* (2013.01);
(Continued)

(58) Field of Classification Search
CPC ............. A61B 5/6833; A61B 5/04085; A61B 5/04087; A61B 5/14532; A61B 2560/0443
See application file for complete search history.

(56) References Cited

U.S. PATENT DOCUMENTS 6,377,829 B1   4/2002  Al Ali
6,978,182 B2   12/2005 Mazar et al.
(Continued)

FOREIGN PATENT DOCUMENTS

WO   2017035502 A1   3/2017
WO   2017108215 A1   6/2017

OTHER PUBLICATIONS

International Search Report and Written Opinion issued in PCT/US2019/022539, dated Jun. 25, 2019, 18 pages.

*Primary Examiner* — Gary Jackson
*Assistant Examiner* — Zahed Kabir
(74) *Attorney, Agent, or Firm* — Faegre Drinker Biddle & Reath LLP

(57) ABSTRACT

A medical device configured to be adhesively coupled to an external surface of a subject, and to facilitate physiological monitoring of the subject, includes: a first portion having a housing that at least partially encloses an interior chamber and has a grip portion that has a peanut-like shape; and a second portion including a flexible patch configured to facilitate operably coupling the first portion to the subject. The flexible patch includes third and fourth sensor connections configured to operably interface with the first and second sensor connections, respectively; first and second sensing elements; and a flexible circuit assembly configured to electrically couple the third sensor connection to the first sensing element and the fourth sensor connection to the second sensing element. An adhesive assembly is configured to couple the first portion to the second portion, and includes conductive adhesive portions.

20 Claims, 7 Drawing Sheets

(51) Int. Cl.

| | | |
|---|---|---|
| *A61B 5/259* | (2021.01) | |
| *A61B 5/282* | (2021.01) | |
| *A61B 5/11* | (2006.01) | |
| *A61N 1/04* | (2006.01) | |
| *A61B 5/145* | (2006.01) | |
| *A61M 5/142* | (2006.01) | |
| *A61B 5/1455* | (2006.01) | |
| *A61B 5/1477* | (2006.01) | |

(52) U.S. Cl.
CPC ........... *A61B 5/1118* (2013.01); *A61B 5/1455* (2013.01); *A61B 5/1477* (2013.01); *A61B 5/14532* (2013.01); *A61B 2560/0214* (2013.01); *A61B 2560/0412* (2013.01); *A61B 2560/0425* (2013.01); *A61B 2560/0443* (2013.01); *A61B 2562/164* (2013.01); *A61M 5/14248* (2013.01); *A61N 1/046* (2013.01)

(56) References Cited

U.S. PATENT DOCUMENTS

| | | |
|---|---|---|
| 9,782,132 B2 | 10/2017 | Golda et al. |
| 2008/0214901 A1 | 9/2008 | Gehman et al. |
| 2014/0100432 A1 | 4/2014 | Golda et al. |
| 2016/0183854 A1 | 6/2016 | Lee |
| 2016/0242654 A1 | 8/2016 | Quinlan et al. |
| 2016/0351532 A1 | 12/2016 | Akutsu |
| 2017/0188872 A1 | 7/2017 | Hughes et al. |
| 2017/0303424 A1 | 10/2017 | Bobgan et al. |
| 2017/0340233 A1* | 11/2017 | Kuster ................ A61B 5/6823 |

* cited by examiner

WEARABLE DEVICE TO DISPOSABLE PATCH CONNECTION VIA CONDUCTIVE ADHESIVE

CROSS-REFERENCE TO RELATED APPLICATION

This application claims priority to Provisional Application No. 62/644,272, filed Mar. 16, 2018, which is herein incorporated by reference in its entirety.

TECHNICAL FIELD

The presently disclosed subject matter relates to devices and methods for monitoring a subject's health using one or more medical devices. More specifically, the disclosed subject matter relates to wearable medical devices.

BACKGROUND

Disposable adhesive patches are becoming more interesting for use in affixing external medical devices to subjects, at least partially because they are becoming smaller, are being made with more and more features, and have improved battery life over prior wearable devices. Wearable devices would benefit from having reliable electrical connections between internal electronics and the subject's body. For a disposable patch, it can be challenging to create a good mechanical connection between the functional portions and the adhesive patch, while keeping the design of the disposable patch simple and easy to use for patients.

SUMMARY

In an Example 1, a medical device configured to be adhesively coupled to an external surface of a subject, and configured to facilitate physiological monitoring of the subject, the device comprising: a first portion having a housing that at least partially encloses an interior chamber, the housing comprising an outside surface, the outside surface comprising: a lower outside surface comprising a first interface region, a first sensor connection, and a second sensor connection; and a grip portion, the grip portion comprising a first end section, a second end section, and a middle section disposed between the first end section and the second end section, wherein the grip portion has a peanut-like shape, wherein the first and second end sections are wider than the middle section; a second portion comprising a flexible patch configured to facilitate operably coupling the first portion to the subject, the flexible patch comprising: an upper surface comprising a third sensor connection and a fourth sensor connection, the upper surface including a second interface region corresponding to the first interface region, wherein the third sensor connection is configured to operably interface with the first sensor connection, and wherein the fourth sensor connection is configured to operably interface with the second sensor connection; a lower surface comprising a first sensing element and a second sensing element; and a flexible circuit assembly disposed between the upper and lower surfaces of the second portion, the flexible circuit assembly configured to electrically couple the third sensor connection to the first sensing element and the fourth sensor connection to the second sensing element so that, when the first portion is coupled to the second portion, the first and second sensor connection are operably coupled to the first and second sensing elements, respectively; an adhesive assembly configured to be disposed between the first portion and second portion to removeably couple the first portion to the second portion; and an electronics module configured to be disposed within the interior chamber, wherein the electronics module is electrically coupled to the first and second sensor connections and is configured to receive electrical signals from the first and second sensor connections and determine, based on the received electrical signals, at least one physiological parameter measurement associated with the subject.

In an Example 2, the medical device of Example 1, the grip portion further comprising a plurality of grip structures disposed thereon to facilitate gripping.

In an Example 3, the medical device of either of Examples 1 or 2, the flexible circuit assembly comprising: a first flexible element disposed between the upper and lower surfaces of the second portion, the first flexible circuit element extending between the third sensor connection and the first sensing element; and a second flexible circuit element disposed between the upper and lower surfaces of the second portion, the second flexible circuit element extending between the fourth sensor connection and the second sensing element.

In an Example 4, the medical device of any of Examples 1-3, the adhesive assembly comprising: a first conductive adhesive portion configured to be disposed between the third sensor connection and one of the first and second sensor connections; a second conductive adhesive portion configured to be disposed between the fourth sensor connection and the other one of the first and second sensor connections; and a non-conductive adhesive portion disposed around the first and second conductive adhesive portions.

In an Example 5, the medical device of any of Examples 1-4, further comprising: a third sensing element, a fourth sensing element, a fifth sensor connection, a sixth sensor connection, a seventh sensor connection, and an eighth sensor connection; wherein the lower surface of the second portion includes the third and fourth sensing elements, wherein the lower outside surface of the housing includes the fifth and sixth sensor connections, and wherein the upper surface of the second portion includes the seventh and eighth sensor connections; a third flexible circuit element disposed between the upper and lower surfaces of the second portion, the third flexible circuit element extending between the seventh sensor connection and the third sensing element; and a fourth flexible circuit element disposed between the upper and lower surfaces of the second portion, the fourth flexible circuit element extending between the eighth sensor connection and the fourth sensing element, wherein the fifth sensor connection is configured to operably interface with the seventh sensor connection, and wherein the sixth sensor connection is configured to operably interface with the eighth sensor connection so that, when the first portion is coupled to the second portion, the fifth sensor connection is operably coupled to the third sensing element and the sixth sensor connection is operably coupled to the fourth sensing element.

In an Example 6, the medical device of any of Examples 1-5, further comprising an alignment feature disposed on the upper surface of the second portion, the alignment feature comprising an indication of a border of the second interface region.

In an Example 7, the medical device of any of Examples 1-6, further comprising a disposable cover configured to be removeably disposed over at least a portion of the medical device.

In an Example 8, the medical device of any of Examples 1-7, the electronics module comprising a support structure disposed within the interior chamber, the support structure configured to receive and support an electronics assembly, wherein the support structure comprises an additional alignment feature configured to facilitate accurate alignment of the electronics assembly within the support structure.

In an Example 9, the medical device of any of Examples 1-8, wherein the second portion further comprises at least one sensor port, the at least one sensor port comprising an aperture disposed through at least a portion of the second portion and configured to facilitate exposure of a sensor to the subject, wherein the sensor comprises at least one of a chemical sensor, an acoustic sensor, an optical sensor, and a temperature sensor.

In an Example 10, a medical device configured to be adhesively coupled to an external surface of a subject, and configured to facilitate physiological monitoring of the subject, the device comprising: a first portion having a housing that at least partially encloses an interior chamber, the housing comprising a lower outside surface comprising a first interface region, a first sensor connection, and a second sensor connection; a second portion comprising a flexible patch configured to facilitate operably coupling the first portion to the subject, the flexible patch comprising: an upper surface comprising a third sensor connection and a fourth sensor connection, the upper surface including a second interface region corresponding to the first interface region, wherein the third sensor connection is configured to operably interface with the first sensor connection, and wherein the fourth sensor connection is configured to operably interface with the second sensor connection; a lower surface comprising a first sensing element and a second sensing element; a first flexible circuit element disposed between the upper and lower surfaces of the second portion, the first flexible circuit element extending between the third sensor connection and the first sensing element so that, when the first portion is coupled to the second portion, the first sensor connection is operably coupled to the first sensing element; and a second flexible circuit element disposed between the upper and lower surfaces of the second portion, the second flexible circuit element extending between the fourth sensor connection and the second sensing element so that, when the first portion is coupled to the second portion, the second sensor connection is operably coupled to the second sensing element; an adhesive assembly configured to be disposed between the first portion and second portion to removeably couple the first portion to the second portion, the adhesive assembly comprising: a first conductive adhesive portion configured to be disposed between the third sensor connection and one of the first and second sensor connections; a second conductive adhesive portion configured to be disposed between the fourth sensor connection and the other one of the first and second sensor connections; and a non-conductive adhesive portion disposed around the first and second conductive adhesive portions; and an electronics module configured to be disposed within the interior chamber, wherein the electronics module is electrically coupled to the first and second sensor connections and is configured to receive electrical signals from the first and second sensor connections and determine, based on the received electrical signals, at least one physiological parameter measurement associated with the subject.

In an Example 11, the medical device of Example 10, the housing of the first portion having an outside surface, the outside surface of the housing comprising a grip portion, the grip portion comprising: a peanut-like shape having a first end section, a second end section, and a middle section disposed between the first end section and the second end section, wherein the first and second end sections are wider than the middle section, and wherein the housing is designed such that a plane tangent to the grip portion at any one of a plurality of locations is oriented approximately perpendicularly to a plane corresponding to the lower outside surface of the lower housing; and a plurality of grip structures disposed thereon to facilitate gripping.

In an Example 12, the medical device of either of Examples 10 or 11, further comprising: a third sensing element, a fourth sensing element, a fifth sensor connection, a sixth sensor connection, a seventh sensor connection, and an eighth sensor connection; wherein the lower surface of the second portion includes the third and fourth sensing elements, wherein the lower outside surface of the housing includes the fifth and sixth sensor connections, and wherein the upper surface of the second portion includes the seventh and eighth sensor connections; a third flexible circuit element disposed between the upper and lower surfaces of the second portion, the third flexible circuit element extending between the seventh sensor connection and the third sensing element; and a fourth flexible circuit element disposed between the upper and lower surfaces of the second portion, the fourth flexible circuit element extending between the eighth sensor connection and the fourth sensing element, wherein the fifth sensor connection is configured to operably interface with the seventh sensor connection, and wherein the sixth sensor connection is configured to operably interface with the eighth sensor connection so that, when the first portion is coupled to the second portion, the fifth sensor connection is operably coupled to the third sensing element and the sixth sensor connection is operably coupled to the fourth sensing element.

In an Example 13, the medical device of any of Examples 10-12, further comprising an alignment feature disposed on the upper surface of the second portion, the alignment feature comprising an indication of a border of the second interface region.

In an Example 14, the medical device of any of Examples 10-13, further comprising a disposable cover configured to be removeably disposed over at least a portion of the medical device.

In an Example 15, the medical device of any of Examples 10-14, the electronics module comprising a support structure disposed within the interior chamber, the support structure configured to receive and support an electronics assembly, wherein the support structure comprises an additional alignment feature configured to facilitate accurate alignment of the electronics assembly within the support structure.

In an Example 16, a medical device configured to be adhesively coupled to an external surface of a subject, and configured to facilitate physiological monitoring of the subject, the device comprising: a first portion having a housing that at least partially encloses an interior chamber, the housing comprising an outside surface, the outside surface comprising: a lower outside surface comprising a first interface region, a first sensor connection, and a second sensor connection; and a grip portion, the grip portion comprising a first end section, a second end section, and a middle section disposed between the first end section and the second end section, wherein the grip portion has a peanut-like shape, wherein the first and second end sections are wider than the middle section; a second portion comprising a flexible patch configured to facilitate operably coupling the first portion to the subject, the flexible patch comprising: an upper surface comprising a third sensor connection and a fourth sensor connection, the upper surface including a second interface region corresponding to the first interface region, wherein the third sensor connection is configured to operably interface with the first sensor connection, and wherein the fourth sensor connection is configured to operably interface with the second sensor connection; a lower surface comprising a first sensing element and a second sensing element; and a flexible circuit assembly disposed between the upper and lower surfaces of the second portion, the flexible circuit assembly configured to electrically couple the third sensor connection to the first sensing element and the fourth sensor connection to the second sensing element so that, when the first portion is coupled to the second portion, the first and second sensor connection are operably coupled to the first and second sensing elements, respectively; an adhesive assembly configured to be disposed between the first portion and second portion to removeably couple the first portion to the second portion; and an electronics module configured to be disposed within the interior chamber, wherein the electronics module is electrically coupled to the first and second sensor connections and is configured to receive electrical signals from the first and second sensor connections and determine, based on the received electrical signals, at least one physiological parameter measurement associated with the subject.

In an Example 17, the medical device of Example 16, the grip portion further comprising a plurality of grip structures disposed thereon to facilitate gripping.

In an Example 18, the medical device of Example 16, the flexible circuit assembly comprising: a first flexible element disposed between the upper and lower surfaces of the second portion, the first flexible circuit element extending between the third sensor connection and the first sensing element; and a second flexible circuit element disposed between the upper and lower surfaces of the second portion, the second flexible circuit element extending between the fourth sensor connection and the second sensing element.

In an Example 19, the medical device of Example 16, the adhesive assembly comprising: a first conductive adhesive portion configured to be disposed between the third sensor connection and one of the first and second sensor connections; a second conductive adhesive portion configured to be disposed between the fourth sensor connection and the other one of the first and second sensor connections; and a non-conductive adhesive portion disposed around the first and second conductive adhesive portions.

In an Example 20, the medical device of claim 16, further comprising: a third sensing element, a fourth sensing element, a fifth sensor connection, a sixth sensor connection, a seventh sensor connection, and an eighth sensor connection; wherein the lower surface of the second portion includes the third and fourth sensing elements, wherein the lower outside surface of the housing includes the fifth and sixth sensor connections, and wherein the upper surface of the second portion includes the seventh and eighth sensor connections; a third flexible circuit element disposed between the upper and lower surfaces of the second portion, the third flexible circuit element extending between the seventh sensor connection and the third sensing element; and a fourth flexible circuit element disposed between the upper and lower surfaces of the second portion, the fourth flexible circuit element extending between the eighth sensor connection and the fourth sensing element, wherein the fifth sensor connection is configured to operably interface with the seventh sensor connection, and wherein the sixth sensor connection is configured to operably interface with the eighth sensor connection so that, when the first portion is coupled to the second portion, the fifth sensor connection is operably coupled to the third sensing element and the sixth sensor connection is operably coupled to the fourth sensing element.

In an Example 21, the medical device of Example 16, further comprising an alignment feature disposed on the upper surface of the second portion, the alignment feature comprising an indication of a border of the second interface region.

In an Example 22, the medical device of Example 16, further comprising a disposable cover configured to be removeably disposed over at least a portion of the medical device.

In an Example 23, the medical device of Example 16, the electronics module comprising a support structure disposed within the interior chamber, the support structure configured to receive and support an electronics assembly, wherein the support structure comprises an additional alignment feature configured to facilitate accurate alignment of the electronics assembly within the support structure.

In an Example 24, the medical device of Example 16, wherein the second portion further comprises at least one sensor port, the at least one sensor port comprising an aperture disposed through at least a portion of the second portion and configured to facilitate exposure of a sensor to the subject, wherein the sensor comprises at least one of a chemical sensor, an acoustic sensor, an optical sensor, and a temperature sensor.

In an Example 25, a medical device configured to be adhesively coupled to an external surface of a subject, and configured to facilitate physiological monitoring of the subject, the device comprising: a first portion having a housing that at least partially encloses an interior chamber, the housing comprising a lower outside surface comprising a first interface region, a first sensor connection, and a second sensor connection; a second portion comprising a flexible patch configured to facilitate operably coupling the first portion to the subject, the flexible patch comprising: an upper surface comprising a third sensor connection and a fourth sensor connection, the upper surface including a second interface region corresponding to the first interface region, wherein the third sensor connection is configured to operably interface with the first sensor connection, and wherein the fourth sensor connection is configured to operably interface with the second sensor connection; a lower surface comprising a first sensing element and a second sensing element; a first flexible circuit element disposed between the upper and lower surfaces of the second portion, the first flexible circuit element extending between the third sensor connection and the first sensing element so that, when the first portion is coupled to the second portion, the first sensor connection is operably coupled to the first sensing element; and a second flexible circuit element disposed between the upper and lower surfaces of the second portion, the second flexible circuit element extending between the fourth sensor connection and the second sensing element so that, when the first portion is coupled to the second portion, the second sensor connection is operably coupled to the second sensing element; an adhesive assembly configured to be disposed between the first portion and second portion to removeably couple the first portion to the second portion, the adhesive assembly comprising: a first conductive adhesive portion configured to be disposed between the third sensor connection and one of the first and second sensor connections; a second conductive adhesive portion configured to be disposed between the fourth sensor connection and the other one of the first and second sensor connections; and a non-conductive adhesive portion disposed around the conductive adhesive portions; an electronics module configured to be disposed within the interior chamber, wherein the electronics module is electrically coupled to the first and second sensor connections and is configured to receive electrical signals from the first and second sensor connections and determine, based on the received electrical signals, at least one physiological parameter measurement associated with the subject.

In an Example 26, the medical device of Example 25, the housing of the first portion having an outside surface, the outside surface of the housing comprising a grip portion, the grip portion comprising: a peanut-like shape having a first end section, a second end section, and a middle section disposed between the first end section and the second end section, wherein the first and second end sections are wider than the middle section, and wherein the housing is designed such that a plane tangent to the grip portion at any one of a plurality of locations is oriented approximately perpendicularly to a plane corresponding to the lower outside surface of the lower housing; and a plurality of grip structures disposed thereon to facilitate gripping.

In an Example 27, the medical device of Example 25, further comprising: a third sensing element, a fourth sensing element, a fifth sensor connection, a sixth sensor connection, a seventh sensor connection, and an eighth sensor connection; wherein the lower surface of the second portion includes the third and fourth sensing elements, wherein the lower outside surface of the housing includes the fifth and sixth sensor connections, and wherein the upper surface of the second portion includes the seventh and eighth sensor connections; a third flexible circuit element disposed between the upper and lower surfaces of the second portion, the third flexible circuit element extending between the seventh sensor connection and the third sensing element; and a fourth flexible circuit element disposed between the upper and lower surfaces of the second portion, the fourth flexible circuit element extending between the eighth sensor connection and the fourth sensing element, wherein the fifth sensor connection is configured to operably interface with the seventh sensor connection, and wherein the sixth sensor connection is configured to operably interface with the eighth sensor connection so that, when the first portion is coupled to the second portion, the fifth sensor connection is operably coupled to the third sensing element and the sixth sensor is operably coupled to the fourth sensing element.

In an Example 28, the medical device of Example 25, further comprising an alignment feature disposed on the upper surface of the second portion, the alignment feature comprising an indication of a border of the second interface region.

In an Example 29, the medical device of Example 25, further comprising a disposable cover configured to be removeably disposed over at least a portion of the medical device.

In an Example 30, the medical device of Example 25, the electronics module comprising a support structure disposed within the interior chamber, the support structure configured to receive and support an electronics assembly, wherein the support structure comprises an additional alignment feature configured to facilitate accurate alignment of the electronics assembly within the support structure.

In an Example 31, a medical device configured to be adhesively coupled to an external surface of a subject, and configured to facilitate physiological monitoring of the subject, the device comprising: a first portion having a housing that at least partially encloses an interior chamber, the housing comprising an outside surface, the outside surface comprising: a lower outside surface comprising a first interface region, a first sensor connection, and a second sensor connection; and a grip portion, the grip portion comprising a first end section, a second end section, and a middle section disposed between the first end section and the second end section, wherein the grip portion has a peanut-like shape, wherein the first and second end sections are wider than the middle section; and an electronics module configured to be disposed within the interior chamber, wherein the electronics module is electrically coupled to the first and second sensor connections and is configured to receive electrical signals from the first and second sensor connections and determine, based on the received electrical signals, at least one physiological parameter measurement associated with the subject; wherein the first portion is configured to be removeably coupled to a second portion, the second portion comprising a flexible patch configured to facilitate operably coupling the first portion to the subject, the flexible patch comprising: an upper surface comprising a third sensor connection and a fourth sensor connection, the upper surface including a second interface region corresponding to the first interface region, wherein the third sensor connection is configured to operably interface with the first sensor connection, and wherein the fourth sensor connection is configured to operably interface with the second sensor connection; a lower surface comprising a first sensing element and a second sensing element; and a flexible circuit assembly disposed between the upper and lower surfaces of the second portion, the flexible circuit assembly configured to electrically couple the third sensor connection to the first sensing element and the fourth sensor connection to the second sensing element so that, when the first portion is coupled to the second portion, the first and second sensor connection are operably coupled to the first and second sensing elements, respectively.

In an Example 32, the medical device of Example 31, further comprising an adhesive assembly configured to be disposed between the first portion and the second portion to removeably couple the first portion to the second portion, the adhesive assembly comprising: a first conductive adhesive portion configured to be disposed between the third sensor connection and one of the first and second sensor connections; a second conductive adhesive portion configured to be disposed between the fourth sensor connection and the other one of the first and second senor connections; and a non-conductive adhesive portion disposed around the first and second conductive adhesive portions.

In an Example 33, the medical device of Example 31, wherein the second portion further comprises at least one sensor port, the at least one sensor port comprising an aperture disposed through at least a portion of the second portion and configured to facilitate exposure of a sensor to the subject, wherein the sensor comprises at least one of a chemical sensor, an acoustic sensor, an optical sensor, and a temperature sensor.

In an Example 34, the medical device of Example 33, the sensor comprising a chemical sensor, the chemical sensor comprising a reagent disposed within the sensor port and a reaction-detection mechanism disposed in the first portion of the medical device.

In an Example 35, the medical device of Example 31, further comprising an alignment feature disposed on the upper surface of the second portion.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

Figure 1:
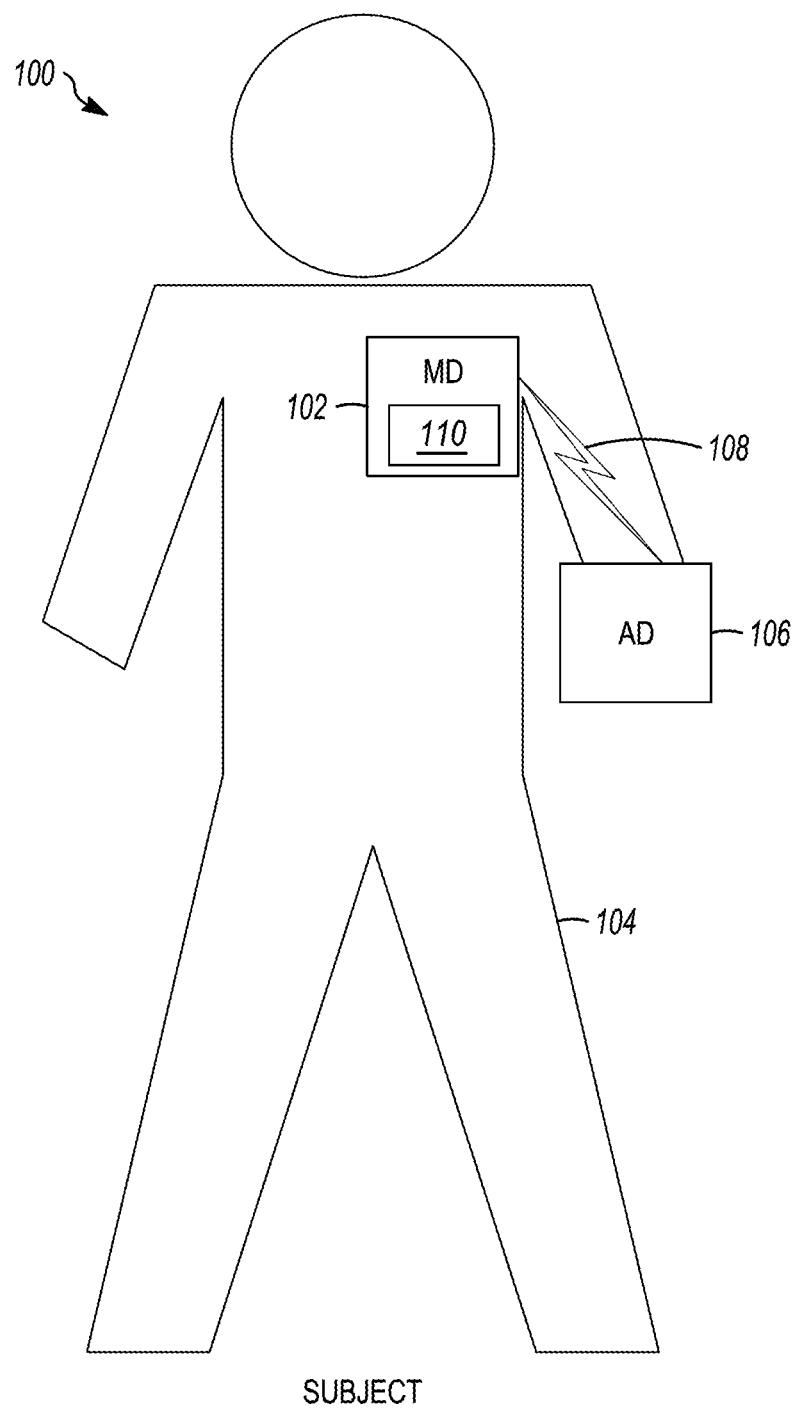
FIG. 1 is a schematic diagram of an illustrative medical system, in accordance with embodiments of the subject matter disclosed herein.

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

As the terms are used herein with respect to measurements (e.g., dimensions, characteristics, attributes, components, etc.), and ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

As used herein, the term "based on" is not meant to be restrictive, but rather indicates that a determination, identification, prediction, calculation, and/or the like, is performed by using, at least, the term following "based on" as an input. For example, predicting an outcome based on a particular piece of information may additionally, or alternatively, base the same determination on another piece of information.

DETAILED DESCRIPTION

Embodiments include a medical device configured to be adhesively coupled to an external surface of a subject, and configured to facilitate physiological monitoring of the subject. In embodiments, the medical device includes a first portion that includes a housing containing the electronics, and a second portion to which the first portion can be removeably coupled. The second portion includes a flexible material configured to adhere to the subject so as to facilitate operably coupling the first portion to the subject.

FIG. 1 shows an illustrative medical system 100, in accordance with embodiments of the disclosure. As shown in FIG. 1, the medical system 100 includes a mobile device (MD) 102 configured to be positioned adjacent (e.g., on or near) the body of a subject 104, and an additional device (AD) 106, which is communicatively coupled to the MD 102 via a communication link 108. In the illustrated embodiments, the medical system 100 is operably coupled to the subject 104, and the MD 102 and the AD 106 are configured to communicate with one another over the communication link 108. For example, in embodiments, the MD 102 may be a medical device configured to be adhesively coupled to an external surface of the subject 104 and configured to facilitate physiological monitoring of the subject 104, as described herein.

The subject 104 may be a human, a dog, a pig, and/or any other animal having physiological parameters that can be recorded. For example, in embodiments, the subject 104 may be a human patient. According to embodiments, the AD 106 may be, be similar to, include, be included within, or be integrated with the MD 102. Additionally or alternatively, in embodiments, the MD 102 and/or the AD 106 may be configured to communicate with any number of different devices, systems, users, and/or the like.

In embodiments, the communication link 108 may be, or include, a wired link (e.g., a link accomplished via a physical connection) and/or a wireless communication link such as, for example, a short-range radio link, such as Bluetooth, IEEE 802.11, near-field communication (NFC), WiFi, a proprietary wireless protocol, and/or the like. The term "communication link" may refer to an ability to communicate some type of information in at least one direction between at least two devices, and should not be understood to be limited to a direct, persistent, or otherwise limited communication channel. That is, according to embodiments, the communication link 108 may be a persistent communication link, an intermittent communication link, an ad-hoc communication link, and/or the like. The communication link 108 may refer to direct communications between the MD 102 and the AD 106, and/or indirect communications that travel between the MD 102 and the AD 106 via at least one other device (e.g., a repeater, router, hub, and/or the like). The communication link 108 may facilitate uni-directional and/or bi-directional communication between the MD 102 and the AD 106. Data and/or control signals may be transmitted between the MD 102 and the AD 106 to coordinate the functions of the MD 102 and/or the AD 106. In embodiments, subject data may be downloaded from one or more of the MD 102 and the AD 106 periodically or on command. The clinician and/or the subject may communicate with the MD 102 and/or the AD 106, for example, to acquire subject data or to initiate, terminate and/or modify recording and/or therapy.

In embodiments, the MD 102 and/or the AD 106 may provide one or more of the following functions with respect to a subject: sensing, data analysis, and therapy. For example, in embodiments, the MD 102 and/or the AD 106 may be used to measure any number of a variety of physiological, device, subjective, and/or environmental parameters associated with the subject 104, using electrical, mechanical, and/or chemical means. The MD 102 and/or the AD 106 may be configured to automatically gather data, gather data upon request (e.g., input provided by the subject, a clinician, another device, and/or the like), and/or any number of various combinations and/or modifications thereof. As is illustrated in the case of the MD 102, the MD 102 (and/or AD 106) may include an electronics assembly 110 configured to perform and/or otherwise facilitate any number of aspects of various functions.

The MD 102 and/or AD 106 may be configured to detect a variety of physiological signals that may be used in connection with various diagnostic, therapeutic and/or monitoring implementations. For example, the MD 102 and/or AD 106 may include sensors or circuitry for detecting respiratory system signals, cardiac system signals, heart sounds, signals related to patient activity. Sensors and associated circuitry may be incorporated in connection with the MD 102 and/or AD 106 for detecting one or more body movement or body posture and/or position related signals.

For example, accelerometers and/or GPS devices may be employed to detect patient activity, patient location, body orientation, and/or torso position. Environmental sensors may, for example, be configured to obtain information about the external environment (e.g., temperature, air quality, humidity, carbon monoxide level, oxygen level, barometric pressure, light intensity, sound, and/or the like) surrounding the subject 104. In embodiments, the MD 102 and/or the AD 106 may be configured to measure any number of other parameters relating to the human body, such as temperature (e.g., a thermometer), blood pressure (e.g., a sphygmomanometer), blood characteristics (e.g., glucose levels), body weight, physical strength, mental acuity, diet, heart characteristics, relative geographic position (e.g., a Global Positioning System (GPS)), and/or the like. Derived parameters may also be monitored using the MD 102 and/or AD 106.

According to embodiments, for example, the MD 102 may include one or more sensing electrodes configured to contact the body (e.g., the skin) of a subject 104 and to, in embodiments, obtain cardiac electrical signals. In embodiments, the MD 102 may include a motion sensor configured to generate an acceleration signal and/or acceleration data, which may include the acceleration signal, information derived from the acceleration signal, and/or the like. A "motion sensor," as used herein, may be, or include, any type of accelerometer, gyroscope, inertial measurement unit (IMU), and/or any other type of sensor or combination of sensors configured to measure changes in acceleration, angular velocity, and/or the like.

The MD 102 and/or the AD 106 may be configured to store data related to the physiological, device, environmental, and/or subjective parameters and/or transmit the data to any number of other devices in the system 100. In embodiments, the MD 102 and/or the AD 106 may be configured to analyze data and/or act upon the analyzed data. For example, the MD 102 and/or the AD 106 may be configured to modify therapy, perform additional monitoring, and/or provide alarm indications based on the analysis of the data.

In embodiments, the MD 102 and/or the AD 106 may be configured to provide therapy. For example, the MD 102 may be configured to communicate with implanted stimulation devices, infusion devices, and/or the like, to facilitate delivery of therapy. The AD 106 may be, include, or be included in a medical device (external and/or implanted) that may be configured to deliver therapy. Therapy may be provided automatically and/or upon request (e.g., an input by the subject 104, a clinician, another device or process, and/or the like). The MD 102 and/or the AD 106 may be programmable in that various characteristics of their sensing, therapy (e.g., duration and interval), and/or communication may be altered by communication between the devices 102 and 106 and/or other components of the system 100.

According to embodiments, the AD 106 may include any type of medical device, any number of different components of an implantable or external medical system, a mobile device, a mobile device accessory, and/or the like. In embodiments, the AD 106 may include a mobile device, a mobile device accessory such as, for example, a device having an electrocardiogram (ECG) module, a programmer, a server, and/or the like. In embodiments, the AD 106 may include a medical device. That is, for example, the AD 106 may include a control device, a monitoring device, a pacemaker, an implantable cardioverter defibrillator (ICD), a cardiac resynchronization therapy (CRT) device and/or the like, and may be an implantable medical device known in the art or later developed, for providing therapy and/or diagnostic data about the subject 104 and/or the MD 102. In various embodiments, the AD 106 may include both defibrillation and pacing/CRT capabilities (e.g., a CRT-D device). In embodiments, the AD 106 may be implanted subcutaneously within an implantation location or pocket in the patient's chest or abdomen and may be configured to monitor (e.g., sense and/or record) physiological parameters associated with the patient's heart. In embodiments, the AD 106 may be an implantable cardiac monitor (ICM) (e.g., an implantable diagnostic monitor (IDM), an implantable loop recorder (ILR), etc.) configured to record physiological parameters such as, for example, one or more cardiac electrical signals, heart sounds, heart rate, blood pressure measurements, oxygen saturations, and/or the like.

In various embodiments, the AD 106 may be a device that is configured to be portable with the subject 104, e.g., by being integrated into a vest, belt, harness, sticker; placed into a pocket, a purse, or a backpack; carried in the subject's hand; and/or the like, or otherwise operably (and/or physically) coupled to the subject 104. The AD 106 may be configured to monitor (e.g., sense and/or record) physiological parameters associated with the subject 104 and/or provide therapy to the subject 104. For example, the AD 106 may be, or include, a wearable cardiac defibrillator (WCD) such as a vest that includes one or more defibrillation electrodes. In embodiments, the AD 106 may include any number of different therapy components such as, for example, a defibrillation component, a drug delivery component, a neurostimulation component, a neuromodulation component, a temperature regulation component, and/or the like. In embodiments, the AD 106 may include limited functionality, e.g., defibrillation shock delivery and communication capabilities, with arrhythmia detection, classification and/or therapy command/control being performed by a separate device.

The illustrative medical system 100 shown in FIG. 1 is not intended to suggest any limitation as to the scope of use or functionality of embodiments of the present disclosure. The illustrative medical system 100 should not be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the subject matter disclosed herein.

Various components depicted in FIG. 1 may operate together to form the medical system 100, which may be, for example, a computerized patient management and monitoring system. In embodiments, the system 100 may be designed to assist in monitoring the subject's condition, managing the subject's therapy, and/or the like. An illustrative patient management and monitoring system is the LATITUDE® patient management system from Boston Scientific Corporation, Natick Mass. Illustrative aspects of a patient management and monitoring system are described in ADVANCED PATIENT MANAGEMENT SYSTEM INCLUDING INTERROGATOR/TRANSCEIVER UNIT, U.S. Pat. No. 6,978,182 to Mazar et al., the entirety of which is hereby incorporated by reference herein.

Figure 2:
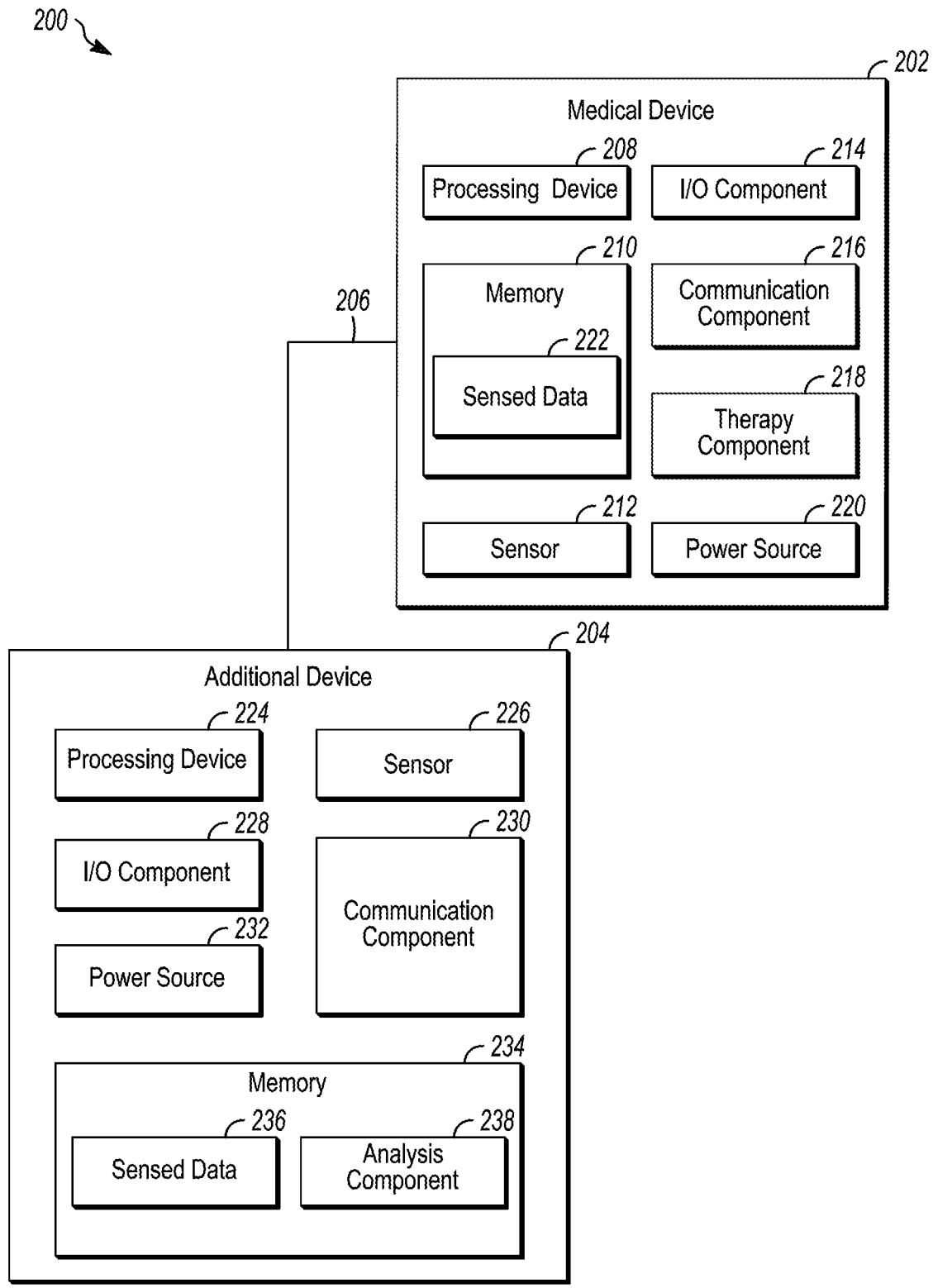
FIG. 2 is a block diagram depicting an illustrative operating environment, in accordance with embodiments of the subject matter disclosed herein.

FIG. 2 is a block diagram depicting an illustrative operating environment 200, in accordance with embodiments of the subject matter disclosed herein. According to embodiments, the operating environment 200 may be, be similar to, include, be included in, or otherwise correspond to the system 100 depicted in FIG. 1. As shown in FIG. 2, the illustrative operating environment 200 includes a medical device (MD) 202 configured to communicate with an additional device (AD) 204 via a communication link 206. In embodiments, the operating environment 200 may include the MD 202 without including an AD 204, and/or include another device. Additionally or alternatively, the operating environment 200 may include more than one MD 202 and/or more than one AD 204. According to embodiments, the MD 202 may be, be similar to, include, or be included in the MD 102 depicted in FIG. 1; the AD 204 may be, be similar to, include, or be included in the AD 106 depicted in FIG. 1; and, the communication link 206 may be, be similar to, include, or be included in the communication links 108 depicted in FIG. 1.

According to embodiments illustrated in FIG. 2, the MD 202 includes a processing device 208, a memory 210, a sensor 212, an input/output (I/O) component 214, a communication component 216, a therapy component 218, and/or a power source 220. Any number of the different illustrated components may represent one or more of said components. The processing device 208 may include, for example, one or more processing units, one or more pulse generators, one or more controllers, one or more microcontrollers, and/or the like. The processing device 208 may be any arrangement of electronic circuits, electronic components, processors, program components and/or the like configured to store and/or execute programming instructions, to direct the operation of the other functional components of the MD 202, to perform processing on any sounds sensed by the sensor 212, to direct the therapy component 218 to provide a therapy, and/or the like, and may be implemented, for example, in the form of any combination of hardware, software, and/or firmware.

In embodiments, the processing device 208 may be, include, or be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. According to embodiments, the processing device 208 may include a processing unit configured to communicate with memory 210 to execute computer-executable instructions stored in the memory 210. As indicated above, although the processing device 208 is referred to herein in the singular, the processing device 208 may be implemented in multiple instances, distributed across multiple sensing devices, instantiated within multiple virtual machines, and/or the like.

The processing device 208 may also be configured to store information in the memory 210 and/or access information from the memory 210. For example, the processing device 208 may be configured to store data obtained by the sensor 212 as sensed data 222 in memory 210. In embodiments, the memory 210 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory stores computer-executable instructions for causing the processor to implement aspects of embodiments of system components discussed herein and/or to perform aspects of embodiments of methods and procedures discussed herein.

Computer-executable instructions stored on memory 210 may include, for example, computer code, machine-useable instructions, and the like such as, for example, program components capable of being executed by one or more processors associated with the computing device. Program components may be programmed using any number of different programming environments, including various languages, development kits, frameworks, and/or the like. Some or all of the functionality contemplated herein may also, or alternatively, be implemented in hardware and/or firmware.

In embodiments, the sensor 212 may sense, at one or more times and/or at one or more locations, physiological parameters, device parameters, and/or environmental parameters, which may then be saved as sensed data 222 on memory 210 and/or transmitted to the AD 204. Physiological parameters may include, for example, cardiac electrical signals, respiratory signals, heart sounds, chemical parameters, body temperature, activity parameters, and/or the like. Device parameters may include any number of different parameters associated with a state of the MD 202 and/or any other device (e.g., the AD 204) and may include, for example, battery life, end-of-life indicators, processing metrics, and/or the like. Environmental parameters may include particulates, ultraviolet light, volatile organic compounds, and/or the like in the environment. The physiological parameters may include respiratory parameters (e.g., rate, depth, rhythm), motion parameters, (e.g., walking, running, falling, gait, gait rhythm), facial expressions, swelling, heart sounds, sweat, sweat composition (e.g., ammonia, pH, potassium, sodium, chloride), exhaled air composition, Electrocardiography (ECG) parameters, electroencephalogram (EEG) parameters, Electromyography (EMG) parameters, and/or the like. Additionally or alternatively, location data indicative of the location of the sensor 212 may be saved as sensed data 222 and/or transmitted to the AD 204. While one sensor 212 is depicted as being included in the MD 202, the MD 202 may include multiple sensors 212.

The I/O component 214 may include and/or be coupled to a user interface configured to present information to a user or receive indication from a user. For example, the I/O component 214 may include and/or be coupled to a display device, a speaker, a printing device, a light emitting diode (LED), and/or the like, and/or an input component such as, for example, a button, a microphone, a joystick, a satellite dish, a scanner, a printer, a wireless device, a keyboard, a pen, a voice input device, a touch input device, a touchscreen device, an interactive display device, a mouse, and/or the like. In embodiments, the I/O component 214 may be used to present and/or provide an indication of any of the data sensed and/or produced by the MD 202.

The communication component 216 may be configured to communicate (i.e., send and/or receive signals) with the AD 204 and/or other devices. In embodiments, the communication component 216 may be configured to send sensed data 222 to the AD 204 in response to sensing one or more sounds produced by a body part. Additionally or alternatively, the communication component 216 may be configured to receive signals from the AD 204 to, for example, supplement the sensed data 222 sensed by the sensor 212. The communication component 216 may include, for example, circuits, program components, and one or more transmitters and/or receivers for communicating wirelessly with one or more other devices such as, for example, the AD 204. According to various embodiments, the communication component 216 may include one or more transmitters, receivers, transceivers, transducers, and/or the like, and may be configured to facilitate any number of different types of wireless communication such as, for example, radio-frequency (RF) communication, microwave communication, infrared communication, acoustic communication, inductive communication, conductive communication, and/or the like. The communication component 216 may include any combination of hardware, software, and/or firmware configured to facilitate establishing, maintaining, and using any number of communication links.

The therapy component 218 may be configured to delivery therapy in response to one or more sensed and/or derived signals. In embodiments, the therapy component 218 may include any number of different therapy components such as, for example, a drug delivery component, an inhaler component, a nebulizer component, defibrillation component, a neurostimulation component, a neuromodulation component, a temperature regulation component, and/or the like.

The power source 220 provides electrical power to the other operative components (e.g., the processing device 208, the memory 210, the sensor 212, the I/O component 214, the communication component 216, and/or the therapy component 218), and may be any type of power source suitable for providing the desired performance and/or longevity requirements of the MD 202. In various embodiments, the power source 220 may include one or more batteries, which may be rechargeable (e.g., using an external energy source). For example, in embodiments, the AD 204 and/or another device may be used to charge the power source 220, transfer power to the power source 220 and/or the like. The power source 220 may include one or more capacitors, energy conversion mechanisms, and/or the like. Additionally or alternatively, the power source 220 may harvest energy from a subject (e.g., the subject 104) (e.g. motion, heat, biochemical) and/or from the environment (e.g. electromagnetic). Additionally or alternatively, the power source 220 may harvest energy from an energy source connected to the body, for example, a shoe may receive energy from impact and send the received energy to a power source 220 of the AD 202.

As shown in FIG. 2, the AD 204 includes a processing device 224, a sensor 226, an I/O component 228, a communication component 230, a power source 232, and/or a memory 234. The processing device 224 may include, for example, a processing unit, a pulse generator, a controller, a microcontroller, and/or the like. The processing device 224 may be any arrangement of electronic circuits, electronic components, processors, program components and/or the like configured to store and/or execute programming instructions, to direct the operation of the other functional components of the AD 204, to image a body part of a subject using sounds, and/or perform any number of other functions such as, for example, perform ECG detection, EEG detection, EMG detection, arrhythmia detection, respiratory functionality detection, and/or classification algorithms, to store physiologic data obtained by the sensor 226 as sensed data 236 on the memory 234, and/or the like, and may be implemented, for example, in the form of any combination of hardware, software, and/or firmware.

In embodiments, the processing device 224 may be, include, or be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. According to embodiments, the processing device 224 may include a processing unit configured to communicate with memory to execute computer-executable instructions stored in the memory. Although the processing device 224 is referred to herein in the singular, the processing device 224 may be implemented in multiple instances, distributed across multiple computing devices, instantiated within multiple virtual machines, and/or the like.

The processing device 224 may also be configured to store information in the memory 234 and/or access information from the memory 234. The processing device 224 may execute instructions and perform desired tasks as specified by computer-executable instructions stored in the memory 234. In embodiments, for example, the processing device 224 may be configured to instantiate, by executing instructions stored in the memory 234, an analysis component 238, and/or the like. Additionally or alternatively, the processing device 224 may store any sensed data 236 sensed by the sensor 226 in the memory 234. In embodiments, the processing device 224 may store any sensed data 222 transmitted to the AD 204 from the MD 202 as sensed data 236 in the memory 236. Additionally or alternatively, if the sensed data 236 is transferred from the AD 204 to another device, the processing device 224 may be configured to erase the sensed data 236 from the AD 204 to free-up storage space on the memory 234.

The sensor 226 may sense any number of different physiological, device, and/or environmental parameters, which may then be saved as sensed data 236. The I/O component 228 may include and/or be coupled to a user interface configured to present information to a user or receive indication from a user. For example, the I/O component 228 may include and/or be coupled to a display device, a speaker, a printing device, an LED, and/or the like, and/or an input component such as, for example, a button, a microphone, a joystick, a satellite dish, a scanner, a printer, a wireless device, a keyboard, a pen, a voice input device, a touch input device, a touch-screen device, an interactive display device, a mouse, a volatile compound release depot, and/or the like. In embodiments, the I/O component 228 may be used to present and/or provide an indication of any of the data sensed and/or produced by the AD 204 and/or the MD 202. For example, the I/O component 228 may be used to present a representation of an output of a predictive algorithm configured to predict a physiological event (e.g., a predicted value, an alert, an alarm, etc.), a representation of a physiological signal, and/or the like. In embodiments, the I/O component 228 may include one or more visual indicators (e.g., single-color LED lights, multi-color LED lights, a flexible digital display device, and/or the like) configured to provide information to a user (e.g., by illuminating, flashing, displaying data, etc.). Additionally or alternatively, the I/O component 228 may be used to control therapy provided by the MD 202 and/or another device.

The communication component 230 may be configured to communicate (i.e., send and/or receive signals) with the MD 202 and/or any other device. Additionally or alternatively, the communication component 230 may facilitate receiving the sensed data 222 from the MD 202 and/or transmit the sensed data 236 from the AD 204 to the MD 202 and/or to another device for processing and/or storage.

In embodiments, the communication component 230 may include, for example, circuits, program components, and one or more transmitters and/or receivers for communicating wirelessly with one or more other devices such as, for example, the MD 202. According to various embodiments, the communication component 230 may include one or more transmitters, receivers, transceivers, transducers, and/or the like, and may be configured to facilitate any number of different types of wireless communication such as, for example, radio-frequency (RF) communication, microwave communication, infrared or visual spectrum communication, acoustic communication, inductive communication, conductive communication, and/or the like. The communication component 230 may include any combination of hardware, software, and/or firmware configured to facilitate establishing, maintaining, and using any number of communication links.

The power source 232 provides electrical power to the other operative components (e.g., the processing device 224, the sensor 226, the I/O component 228, the communication component 230, and/or the memory 234), and may be any type of power source suitable for providing the desired performance and/or longevity requirements of the AD 204. In various embodiments, the power source 232 may include one or more batteries, which may be rechargeable (e.g., using an external energy source). The power source 232 may include one or more capacitors, energy conversion mechanisms, and/or the like. Additionally or alternatively, the power source 232 may harvest energy from a subject (e.g., the subject 104) (e.g. motion, heat, biochemical) and/or from the environment (e.g. electromagnetic). Additionally or alternatively, the power source 232 may harvest energy from an energy source connected to the body and send the received energy to a power source 232 of the AD 204. In embodiments, the power source 220 may transfer power to the power source 232 (or vice versa) using a wireless or non-wireless connection (e.g., via conduction, induction, radio-frequency, etc.).

In embodiments, the memory 234 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory stores computer-executable instructions for causing the processor to implement aspects of embodiments of system components discussed herein and/or to perform aspects of embodiments of methods and procedures discussed herein.

The memory 234 may store instructions that, when executed by the processing device 224 cause methods and processes to be performed by the AD 204. For example, the processing device 224 may instantiate (e.g., from the memory 234) an analysis component 238. In embodiments, the analysis component 238 may be configured to analyze sensed data 236 by performing any number of different processes such as, for example, filtering, interpolating, and/or the like. In embodiments, the analysis component 238 may be configured to determine, based on the sensed data 236, a likelihood of an occurrence of a physiological event, which may be referred to herein as "predicting an event" and/or the like. In embodiments, for example, the analysis component 238 may be configured to predict an occurrence of a next heart beat (e.g., by predicting a time at which the next heart beat will occur), a cardiac failure, a loss of consciousness, and/or the like.

The analysis component 238 may be configured to implement an algorithm to predict a physiological event associated with a particular body part based on the sensed data 236. In predicting a physiological event, the analysis component 238 may be configured to obtain and/or store a set of information (e.g., sensed data 236) that may be analyzed using one or more adjudication algorithms to predict and/or classify a cardiac episode, audit the effectiveness of a therapy regimen, and/or the like. According to embodiments, prediction data (e.g., classifications, characterization data, sensed data, etc.) can be stored in an adjudication database. In some examples, the characterization data may be sent to a medical device (e.g., MD 202 and/or AD 204) to be stored, displayed, and/or otherwise acted upon. Once a classification (e.g., an arrhythmia classification) has been generated for a particular physiological event or a group of events, it may be possible to provide patients and/or clinicians with many different types of reports related to the event data. It may also be possible for the system to analyze the classifications and/or characterization data to provide programming recommendations for a medical device where certain conditions are present. It may also be possible to query the adjudication database for many different types of information that may be useful to clinicians, researchers, regulators, and/or the like.

In embodiments, the analysis component 238 may utilize information collected by components of a medical system (which may include, e.g., the system 100 depicted in FIG. 1, the operating environment 200 depicted in FIG. 2, etc.), as well as information from other relevant sources, to analyze data related to a subject, and provide predictive assessments of the subject's well-being. In performing this analysis, the analysis component 238 may utilize data collected from a variety of sources, include patient specific physiological and subjective data, medical and historical records (e.g., lab test results, histories of illnesses, etc., drugs currently and previously administered, etc.), information related to population trends, and/or the like.

In embodiments, the analysis component 238 may provide a diagnosis of subject health status and predicted trend based on present and recent historical data. For example, the analysis component 238 may perform probabilistic calculations using currently-collected information combined with regularly-collected historical information to predict subject health degradation. In embodiments, the analysis component 238 may conduct pre-evaluation of the incoming data stream combined with subject historical information and information from subjects with similar disease states. The pre-evaluation system may be based on data derived from working clinical practices and the records of outcomes. The derived data may be processed in a neural network, fuzzy logic system, or equivalent system to reflect the clinical practice. Further, the analysis component 238 may provide means for periodic processing of present and historical data to yield a multidimensional health state indication along with disease trend prediction, next phase of disease progression co-morbidities, and/or inferences about what other possible diseases may be involved. The analysis component 238 may also integrate data collected from internal and external devices to optimize management of overall patient health.

The analysis component 238 may perform any number of different deterministic and probabilistic calculations. In embodiments, the analysis component 238 may include machine-learning capabilities. For example, the analysis component 238 may be implemented via a neural network (or equivalent) system. The analysis component 238 may be partially trained (i.e., the analysis component 238 may be implemented with a given set of preset values and then learn as the advanced patient management system functions) or untrained (i.e., the analysis component 238 may be initiated with no preset values and must learn from scratch as the advanced patient management system functions). In embodiments, the analysis component 238 may continue to learn and adjust as the medical system functions (i.e., in real time), or the analysis component 238 may remain at a given level of learning and only advanced to a higher level of understanding when manually allowed to do so.

The analysis component 238 may be configured to use various algorithms and mathematical modeling such as, for example, trend and statistical analysis, data mining, pattern recognition, cluster analysis, neural networks fuzzy logic, and/or the like. The analysis component 238 may perform deterministic and probabilistic calculations. Deterministic calculations include algorithms for which a clear correlation is known between the data analyzed and a given outcome. Additionally, using the analysis component 238, a bifurcated analysis may be performed for diseases exhibiting similar symptoms. As progressive quantities of data are collected and the understanding of a given disease state advances, disease analysis may be refined such as, for example, where a former singular classification may split into two or more sub-classes.

Any number of various components of the operating environment 200 depicted in FIG. 2 may be communicatively coupled via the communication link 206. The communication link 206 may provide for communications between and among various components of the operating environment 200, such as the MD 202 and the AD 204. The communication link 206 may be, be similar to, include, or be included in the communication link 108 depicted in FIG. 1, and/or any number of different types of communication networks such as, for example, a bus network, a short messaging service (SMS), a local area network (LAN), a wireless LAN (WLAN), a wide area network (WAN), the Internet, a P2P network, custom-designed communication or messaging protocols, and/or the like. The communication link 306 may include a combination of multiple networks, which may be wired and/or wireless.

The illustrative operating environment shown in FIG. 2 is not intended to suggest any limitation as to the scope of use or functionality of embodiments of the present disclosure. The illustrative operating environment 200 also should not be interpreted as having any dependency or requirement related to any single component or combination of components illustrated therein. Additionally, various components depicted in FIG. 2 may be, in embodiments, integrated with various ones of the other components depicted therein (and/or components not illustrated), all of which are considered to be within the ambit of the present disclosure.

Figure 3A:
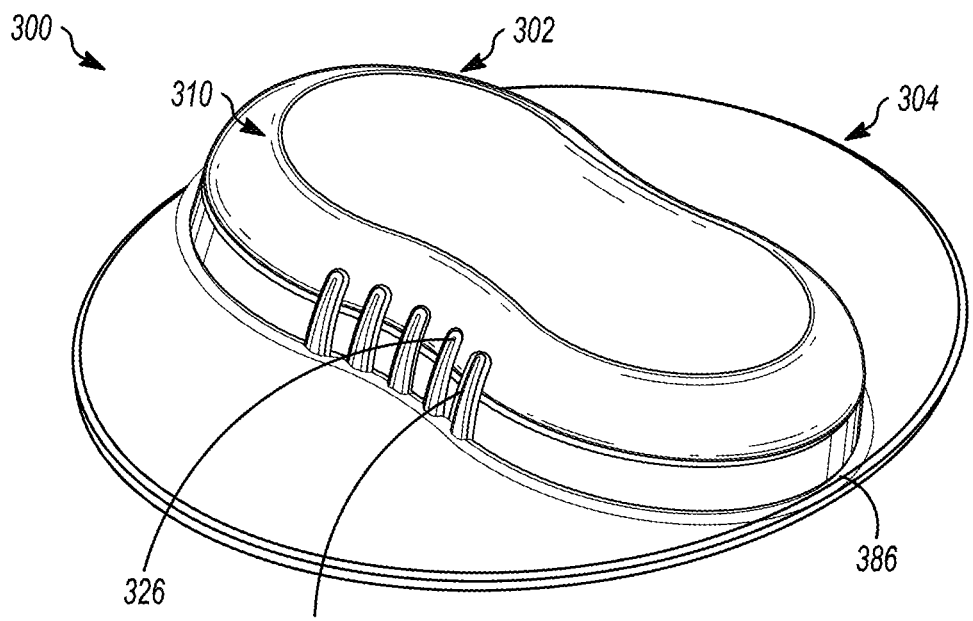
FIG. 3A is a perspective view of an illustrative medical device, in accordance with embodiments of the subject matter disclosed herein.

FIG. 3A depicts an illustrative medical device (MD) 300, in accordance with embodiments of the subject matter disclosed herein. According to embodiments, the MD 300 may be, be similar to, include, be included within, or otherwise correspond to, the MD 102 depicted in FIG. 1 and/or the MD 202 depicted in FIG. 2. As shown in FIG. 3A, the MD 300 includes a first portion 302 configured to be removeably coupled to a second portion 304. According to embodiments, a single first portion 302 may be configured to be removeably coupled to any number of different second portions 304, including second portions 304 with different configurations (e.g., different numbers of sensor connections, etc.). In this manner, embodiments may facilitate providing a device having a durable portion (i.e., the first portion) and a number of different disposable portions (i.e., second portions) that can be used to provide configurations from which to select, based on the number of available second portions. Variations between disposable portions (and, in embodiments, durable portions) may include variations in the number of sensor connections, variations in color, variations in material, variations in size, and/or the like. According to embodiments, the first portion may be at least partially rigid, while the second portion is at least partially flexible. For example, in embodiments, the entire first portion may be rigid, while the entire second portion may be flexible. In embodiments, part of the first portion (e.g., an upper part) may be rigid, while another part (e.g., a lower part) of the first portion may be flexible. In embodiments, a flexibility of the first portion may be change as a function of distance from the lower surface. Any number of other combinations of rigidity and flexibility may be implemented in embodiments of the device 300.

In embodiments, the first portion 302 (which may be referred to, in embodiments, as the durable portion) may be configured to be smaller than the second portion 304 (which may be referred to, in embodiments, as the disposable portion). For example, the first portion 302 may be significantly smaller than the second portion 304 so as to facilitate and/or maximize flexibility of the system, which may improve patient comfort. According to embodiments, the first portion 302 may be configured to be able to be coupled to any number of different types of second portions 304, which may be designed to have any number of different shapes. According to embodiments, the interface between the first and second portions 302 and 304 may be configured to be symmetrical such that the first portion may be, for example, coupled to the second portion 304 in more than one orientation. In other embodiments, the interface may be asymmetrical, thereby facilitating coupling the first and second portions 302 and 304 according to only one orientation.

Figure 3B:
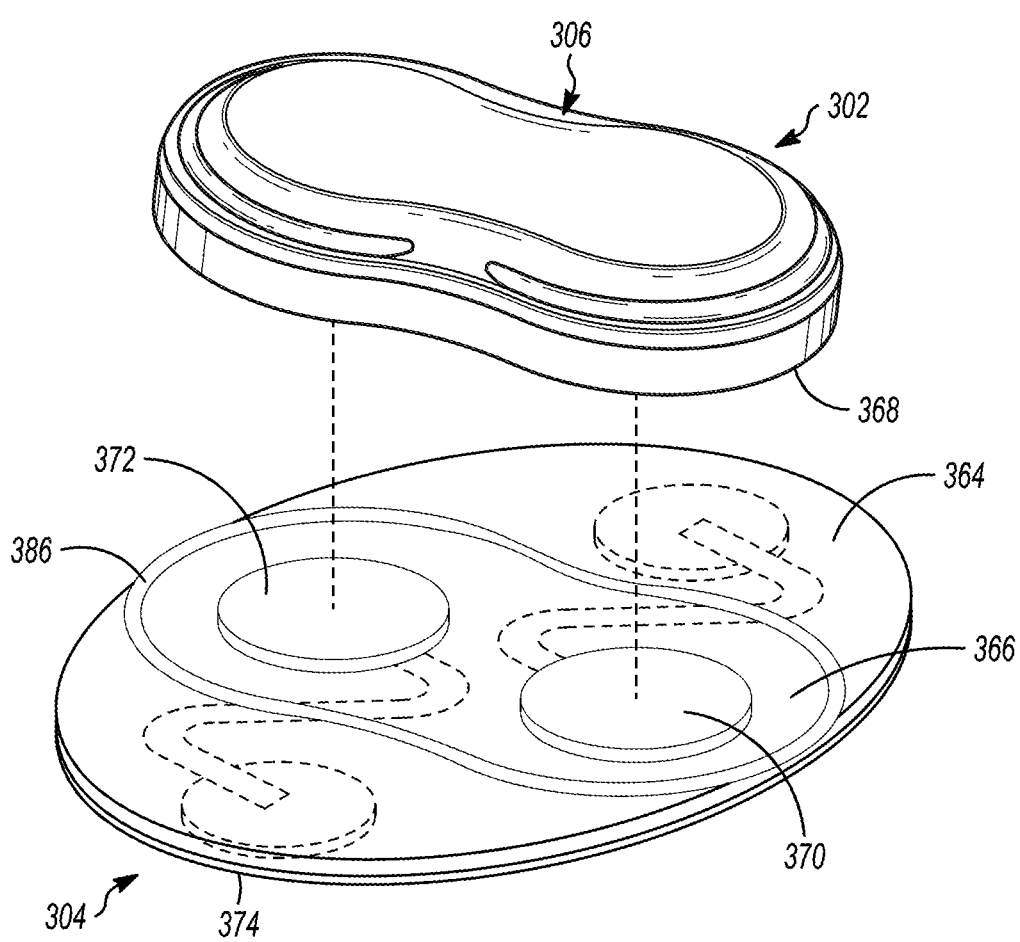
FIG. 3B is a partially exploded perspective view of the illustrative medical device 300 depicted in FIG. 3A, in accordance with embodiments of the subject matter disclosed herein.
Figure 3C:
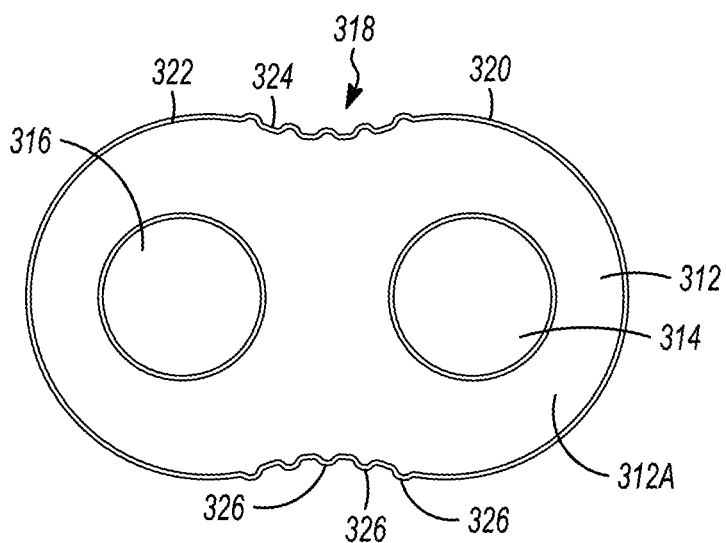
FIG. 3C is a bottom view of a first portion of the illustrative medical device depicted in FIGS. 3A and 3B, in accordance with embodiments of the subject matter disclosed herein.

As shown in FIGS. 3A-3C, the first portion 302 includes a housing 306 that at least partially encloses an interior chamber 308. The first portion 302 may be flexible and/or rigid. The housing 306 includes an outside surface 310 that includes, at least in part, a lower outside surface 312 having a first interface region 312A and one or more sensor connections such as, for example, a first sensor connection 314 and a second sensor connection 316. Although two sensor connections 314 and 316 are illustrated in FIGS. 3A-3C, it should be understood that the first portion 302 may include any number of different sensor connections. In embodiments, the sensor connections may include connections for electrical sensors, chemical sensors, and/or the like. Additionally or alternatively, in embodiments, the outside surface 310 may be formed as one continuous surface, a combination of surfaces, and/or the like. In embodiments, for example, electrical sensor connections may include conductive plates, discs, overlays, and/or the like.

In embodiments, the first portion and/or the second portion may include any number of different user interface features configured to provide information to a user and/or receive information from a user. These user interface features may include input/output (I/O) devices such as, for example, buttons, LEDs, and/or the like.

Figure 3D:
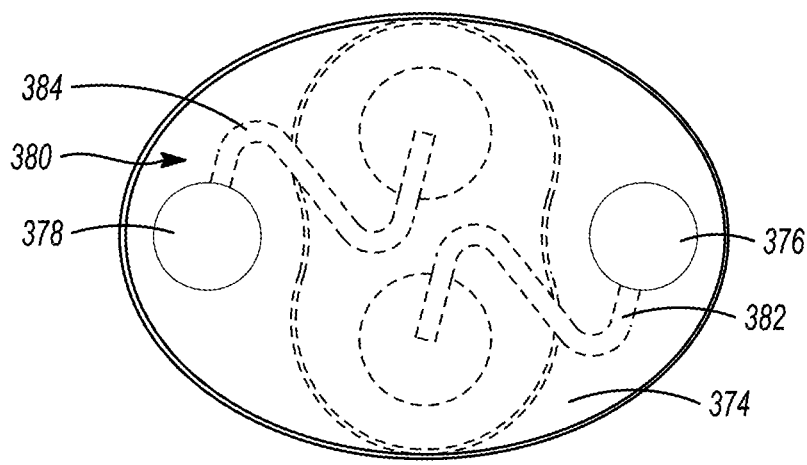
FIG. 3D is a bottom view of a second portion of the illustrative medical device depicted in FIGS. 3A-3C, in accordance with embodiments of the subject matter disclosed herein.
Figure 3E:
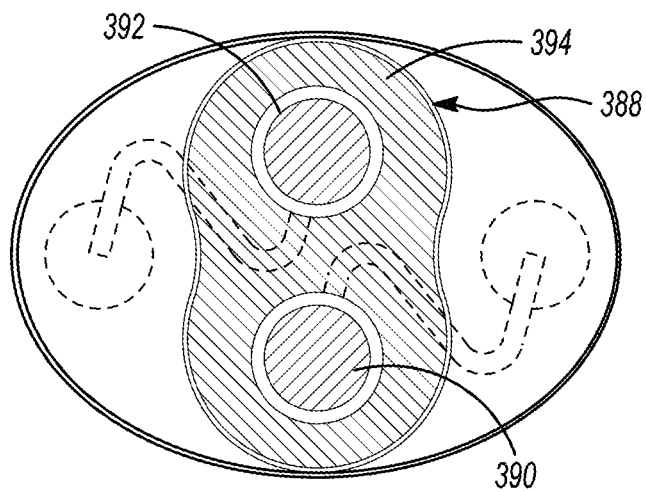
FIG. 3E is a top view of the second portion of the illustrative medical device depicted in FIGS. 3A-3D, in accordance with embodiments of the subject matter disclosed herein.

The outside surface 310 of the housing 306 also includes a grip portion 318, as shown, for example, in FIGS. 3C and 3D. The grip portion 318 of the outside surface 310 may be designed to have a peanut-like shape. That is, for example, the grip portion 318 (and, indeed, the housing 306) may include a first end section 320, a second end section 322, and a middle section 324 disposed between the first end section 320 and the second end section 322. As shown, each of the first and second end sections 320 and 322 is wider than the middle section 324. The grip portion 318 also may include a number of grip structures 326 disposed thereon to facilitate gripping, by a user's hand, the first portion 302 to facilitate, e.g., removing the first portion 302 from the second portion 304 such as, for example, by peeling them apart. According to embodiments, the grip structures 326 may include any number of different types of features configured to facilitate gripping of the first portion 302 by a user. For example, the grip structures 326 may include ribs (as illustrated, and which may be horizontal ribs, vertical ribs, and/or angled ribs), bumps, prizms, texturing, and/or the like.

Figure 3F:
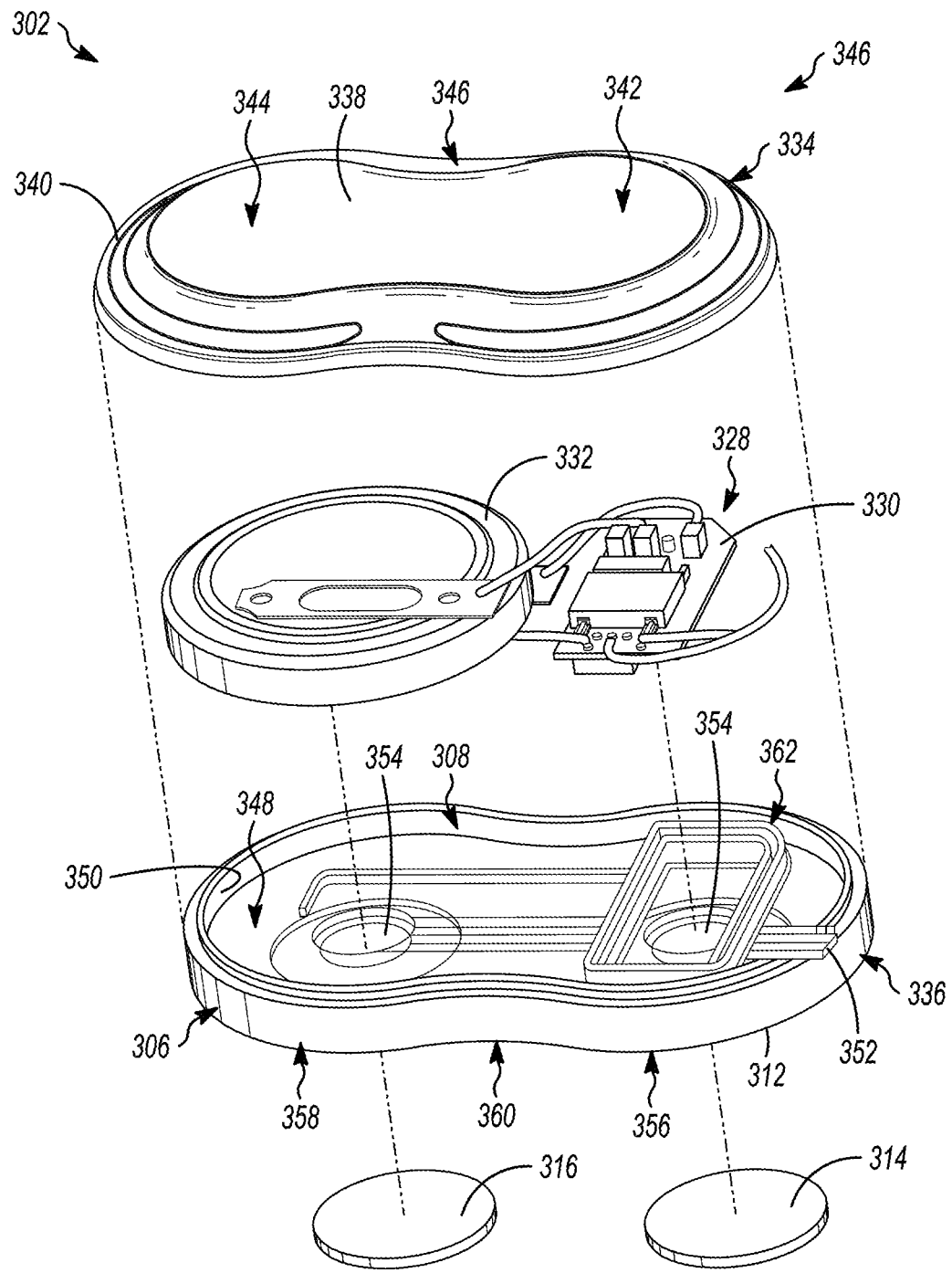
FIG. 3F is an exploded perspective view of the first portion of the illustrative medical device depicted in FIGS. 3A-3E, in accordance with embodiments of the subject matter disclosed herein.

As is further shown in FIG. 3F, for example, the first portion 302 further includes an electronics module 328 configured to be disposed within the interior chamber 308. In embodiments, the electronics module 328 may be, be similar to, be included in, or include the electronics module 110 depicted in FIG. 1, one or more of the components 208, 210, 212, 214, 216, 218, 220, 224, 226, 228, 230, 232, 234, and/or 238 depicted in FIG. 2. For example, in embodiments, the electronics module 328 may be, or include, a printed circuit board (PCB) and/or any number of other circuitry components configured to be electrically coupled to the first and second sensor connections 314 and 316 (and/or other sensor connections), and to receive electrical signals from the first and second sensor connections (and/or other sensor connections) and determine, based on the received electrical signals, any number of a variety of physiological, device, subjective, and/or environmental parameters associated with the subject. For example, in embodiments, the electronics module 328 may be configured to determine at least one physiological parameter measurement associated with the subject. Other sensor arrangements may be used to measure parameters using mechanical, and/or chemical means. The electronics module 328 may be coupled to a power source 332 such as, for example, one or more batteries, capacitors, transducers, and/or the like. In embodiments, for example, the power source 332 may be a 2032 coin cell battery.

The electronics module 328 is enclosed (or at least partially enclosed) within the housing 306. The housing 306 includes a first piece 334 configured to be coupled to a second piece 336. The pieces 334 and 336 may be coupled according to any number of different coupling techniques such as, for example, snapping the two pieces together, welding the two pieces together, clipping them together, and/or the like. As shown, for example, the first piece 334 may include an upper wall 338 that may, in embodiments, be approximately flat. A side wall 340 extends downward from the perimeter of the upper wall 338. In embodiments, the side wall 340 may be curved, approximately straight, or a combination thereof. The side wall 340 (or a portion thereof) may have a peanut-like shape. That is, as shown, the first piece 334 may include a first end section 342, a second end section 344, and a middle section 346 disposed between the first end section 342 and the second end section 344. As shown, each of the first and second end sections 342 and 344 is wider than the middle section 346. As described above, the middle section 346 may be a portion of the grip portion 318 described above and, as such, also may include a number of grip structures 326 (or portions of grip structures) disposed thereon to facilitate gripping.

The second piece 336 may include a lower wall 348 having the lower outside surface 312. A side wall 350 may extend upward from the perimeter of the lower wall 348, as shown in FIG. 3F. In embodiments, the side wall 350 may be curved, approximately straight, or a combination thereof. In embodiments, a charging port 352 (for a mini-USB or other type of power charging connection) may be defined within the side wall 350 (and/or the side wall 340). One or more apertures 354 may be defined in the lower wall 348 (and/or side wall 340, 350, etc.) to facilitate operably coupling sensing assemblies disposed on the second portion 304 of the device 300 to the electronics assembly 328. For example, in embodiments, the apertures 354 may be configured to allow for making an electrical connection between the sensor connections 314 and 316 and the electronics assembly 328. Additionally, as shown in FIG. 3F, the side wall 350 (or a portion thereof) may have a peanut-like shape. That is, as shown, the second piece 336 may include a first end section 356, a second end section 358, and a middle section 360 disposed between the first end section 356 and the second end section 358. As shown, each of the first and second end sections 356 and 358 is wider than the middle section 360. As described above, the middle section 360 may be a portion of the grip portion 318 described above and, as such, also may include a number of grip structures 326 (or portions of grip structures) disposed thereon to facilitate gripping.

According to embodiments, the dimensions and design of the pieces 334 and 336 may be configured to provide a desired amount of volume enclosed within the housing 306. That is, for example, the housing pieces 334 and 336 may be designed such that the electronics assembly 328 and power source 332 fit within the housing 306 while not wasting space (e.g., by optimizing volume usage). As shown in FIG. 3F, the second piece 336 of the housing 306 may include an electronics assembly support structure 362. The electronics assembly 328 is configured to be coupled, on a first side to the electronics assembly support structure 362. In embodiments, the electronics assembly structure 362 may include one or more retaining features, alignment features, and/or the like. The electronics assembly structure 362 may be configured to enhance the available space within the core assembly. For example, the electronics assembly structure 362 may be, be similar to, include, or be included in the core circuitry support structure described in U.S. Publication No. 2017/0303424, filed Apr. 17, 2017, entitled "IMD HAVING A CORE CIRCUITRY SUPPORT STRUCTURE," and assigned to Cardiac Pacemakers, Inc., of St. Paul, Minn., USA, the entirety of which is hereby incorporated herein by reference for all purposes.

The second portion 304 of the medical device 300 includes a flexible patch configured to facilitate operably coupling the first portion 302 to the subject. As shown in FIGS. 3A-3F, for example, the second portion 304 may include an upper surface 364 having an interface region 366 corresponding to an interface region 368 defined in the outside lower surface 312 of the first portion 302. The upper surface 364 also includes a third sensor connection 370 and a fourth sensor connection 372. The second portion also includes a lower surface 374 having a first sensing element 376 and a second sensing element 378. In embodiments, the sensing elements 376 and 378 may be integrated within the surface 374, disposed within apertures defined through the surface 374, disposed on top of the surface 374, disposed below the surface 374, and/or the like. In embodiments, any number of sensing elements may be associated with the surface 374.

A flexible circuit assembly 380 is disposed between the upper and lower surfaces 364 and 374 of the second portion 304, and is configured to electrically couple the third sensor connection 370 and the fourth sensor connection 372 with the first sensing element 376 and the second sensing element 378, respectively. As shown, for example, the flexible circuit assembly 380 may include a first flexible circuit element 382, extending between the third sensor connection 370 and the first sensing element 376; and a second flexible circuit element 384, extending between the fourth sensor connection 370 and the second sensing element 378.

As shown, the second portion 304 also includes an alignment feature 386 disposed on the upper surface 364. In embodiments, the alignment feature 386 may include an indication of at least a portion of the border of the interface region 366. For example, the alignment feature 386 may include a marking on the surface 364 showing one or more parts of the border of the interface region 366. In embodiments, indications may include colors, text, symbols, and/or the like. In embodiments, the alignment feature 386 may be a structure such as, for example, a small wall or flange rising from the surface 364 within which a bottom edge of the first portion 302 fits. Embodiments may include any number of other mechanisms for guiding the placement of the first portion 302 on the upper surface 364 of the second portion 304. For example, in embodiments, the alignment feature 386 may include mechanical features such as corresponding holes and posts, ridges, notches, and/or the like. In embodiments, an alignment tool may be configured to be used to align the first and second portions.

Additionally, in embodiments, the electronics assembly 328 may be configured to determine proper positioning of the device 300 on the subject based on analysis of electrical signals received from the sensor connections and/or sensing elements. For example, in embodiments, impedance measurements may be used to determine an appropriate placement on the subject, which may be determined by identifying a position that satisfies certain criteria associated with one or more signal features of the obtained electrical signals. In embodiments, for example, the criteria may correspond, from a signal processing perspective, to a subcutaneous location in which certain algorithms are designed recognize. That is, for example, the medical device 300 may be used to present an a representation of an output of a predictive algorithm configured to predict a physiological event (e.g., a predicted value, an alert, an alarm, etc.), a representation of a physiological signal, and/or the like. In embodiments, the device 300 may include one or more visual indicators (e.g., single-color LED lights, multi-color LED lights, a flexible digital display device, and/or the like) configured to provide information (e.g., measured parameter information, positioning information/feedback, etc.) to a user (e.g., by illuminating, flashing, displaying data, etc.).

The appropriate position for the device, as determined by the electronics assembly 328, or another computing device, may, for example, be determined in reference to a space associated with a position vector corresponding to a particular measurement location. For example, embodiments of predictive algorithms often are developed using empirical data obtained from medical devices disposed in, on or adjacent to a number of subjects. An example of such a predictive algorithm that may be implemented, in accordance with embodiments of the subject matter disclosed herein is the Heart Logic™ predictive engine available from Boston Scientific, of Marlborough, Mass., USA. Various portions of the Heart Logic™ algorithm that include input from sensors (e.g., heart sounds) were developed using measurements from implanted medical devices corresponding to an approximate location, or relative location, identified within one or more subjects. Accordingly, alignment for use with the Heart Logic™ algorithm may include projecting expected signal measurements into the algorithm-specific space, and/or the like. According to embodiments, any number of other arrangements of medical devices, measurement locations, and/or the like may be utilized in implementations, and may be utilized with any number of different predictive algorithms.

According to embodiments, the second portion 304 may include any number of different types of ports and/or other features configured to facilitate obtaining sensor readings associated with a subject. For example, in embodiments, one or more apertures may be disposed at least partially through the second portion 304. The apertures may be configured to facilitate exposure, to a subject, of a sensing device, reagent, and/or the like.

For example, in embodiments, one or more light-emitting devices (e.g., LEDs, IR emitters, etc.) may be disposed within the first portion 302 and operably coupled to one or more corresponding apertures defined at least partially through the second portion 304, where the apertures provide a path for emitted light to reach the subject. For example, the device 300 may include one or more optically-separated apertures configured to facilitate plethysmography readings so as to facilitate, for example, monitoring pulse oximetry. In embodiments, one or more apertures (e.g., one or more different apertures) may provide light paths for facilitating light detectors disposed in the first portion 302. In embodiments, emitters may be disposed within the second portion 304. According to embodiments, any number of different combinations of electromagnetic emitters and detectors may be disposed in the first and/or second portion. This may, in embodiments, facilitate using the device 300 to monitor pulse oximetry and/or other physiological and/or environmental parameters that can be obtained using an optical sensor. A covering material may be disposed over a lower opening of an aperture, which may serve to protect the emitters and/or detectors, may function as a lens, and/or the like.

According to embodiments, the one or more apertures may be configured to facilitate acoustic sensing and/or thermal sensing. For example, in embodiments, an aperture may provide an acoustic path to an acoustic sensor (e.g., a piezoelectric element) disposed within the first portion 302 and/or the second portion 304. In embodiments, an aperture may include an acoustic-conductive medium such as, for example, a fluid or gel configured to transfer acoustic waves incident on an outside surface of a material disposed over the aperture to an acoustic sensor disposed within the first portion. Similarly, one or more apertures may be configured to transfer, (e.g., through air, a liquid, a gel, etc.) heat energy from the subject to a temperature sensor disposed within the first portion 302. In embodiments, acoustic and/or temperature sensors, or portions thereof, may be disposed within one or more apertures defined in the second portion 304.

As indicated above, embodiments may include one or more chemical sensors. In embodiments, for example, a chemical sensor may include a reagent medium (that is, a medium that hosts a reagent) and an optical sensor configured to detect a change in the appearance of the reagent and/or reagent medium, where the change in appearance results from a chemical reaction between a substance of interest and the reagent. In embodiments, for example, the reagent medium may change color as the substance of interest reacts with the reagent, and the optical sensor may be configured to detect that change in color, characterize the change in color (e.g., detect the color or shades thereof, determine an area within which the color has changed, determine a rate of change of the color, and/or the like). In embodiments, for example, the reagent may be disposed within an aperture defined in the second portion 304, and the optical sensor may be disposed in the first portion 302 such that, when the first and second portions 302 and 304 are coupled, the optical sensor is positioned so that it can detect changes in the reagent. This may facilitate, for example, continuing to perform chemical monitoring after a reagent is consumed, simply by replacing the second portion with a new second portion. Additionally or alternatively, this may facilitate reconfiguring the chemical sensor to test for different substances of interest simply by replacing the second portion 304 with an alternative second portion 304 that has a different reagent disposed therein.

According to embodiments, an adhesive assembly 388 may be configured to be disposed between the first portion 302 and the second portion 304 to removeably couple the first portion 302 to the second portion 304. According to embodiments, the adhesive assembly 388 includes a first conductive adhesive portion 390 configured to be disposed between the third sensor connection 370 and one of the first and second sensor connections 314 and 316; and a second conductive adhesive portion 392 configured to be disposed between the fourth sensor connection 372 and the other one of the first and second sensor connections 314 and 316. The adhesive assembly 388 also may include a non-conductive portion 394. The non-conductive adhesive portion may facilitate electrically isolating sensor connections from each other and from the environment. In embodiments, the adhesive assembly may provide an environmental seal (e.g., a water-tight seal). In embodiments, any number of conductive and/or non-conductive adhesive portions may be included to be used with any number of different sensor connections. According to embodiments, any number of different types of adhesive may be used and, in embodiments, may be offered so that a user may select between adhesives based on one or more associated characteristics such as, for example, comfort, durability, and/or the like.

Additionally, or alternatively, in embodiments, the conductive adhesive may include a z-axis adhesive—that is, an adhesive material that is configured to be conductive in only one direction (generally, in a direction normal to the surface of the adhesive). In this manner, a single type of adhesive (and, in embodiments, a single piece of adhesive) may be used to couple the first portion 302 to the second portion 304, as the electricity will stay approximately within the region of interface of the sensor connections. For example, although a z-axis adhesive may be used in any number of different implementations, it may be particularly useful when there are a large number of sensor connections.

The illustrative medical device 300 shown in FIGS. 3A-3F is not intended to suggest any limitation as to the scope of use or functionality of embodiments of the present disclosure. For example, although it is not illustrated, embodiments may include a disposable cover configured to be removeably disposed over the entire device 300 (or at least a portion of the device) to provide protection and/or the appearance of a simple patch on the subject. The illustrative medical device 300 should not be interpreted as having any dependency or requirement related to any single component or combination of components illustrated therein. Additionally, various components depicted in FIGS. 3A-3F may be, in embodiments, integrated with various ones of the other components depicted therein (and/or components not illustrated), all of which are considered to be within the ambit of the subject matter disclosed herein.

Figure 4A:
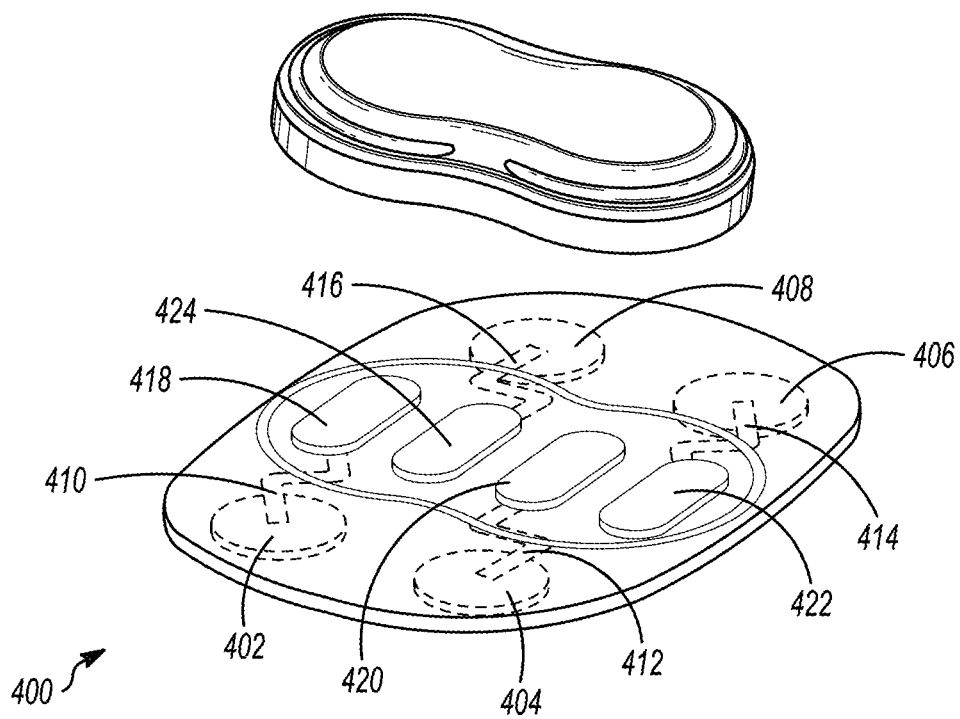
FIG. 4A is a partially-exploded perspective view of an illustrative medical device, in accordance with embodiments of the subject matter disclosed herein.
Figure 4B:
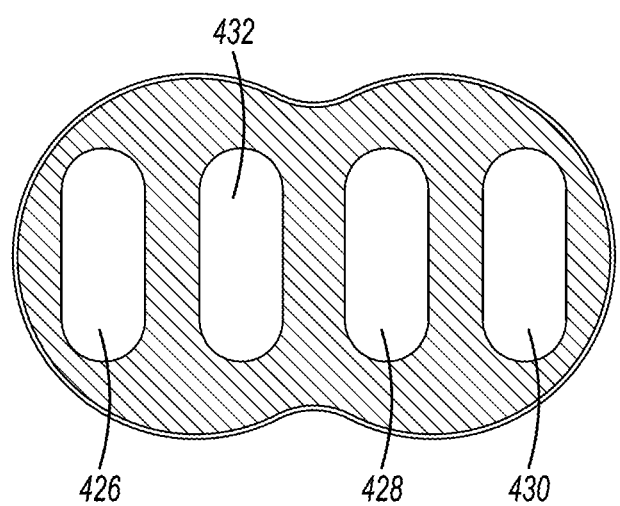
FIG. 4B is a bottom view of a first portion of the illustrative medical device depicted in FIG. 4A, in accordance with embodiments of the subject matter disclosed herein.
Figure 4C:
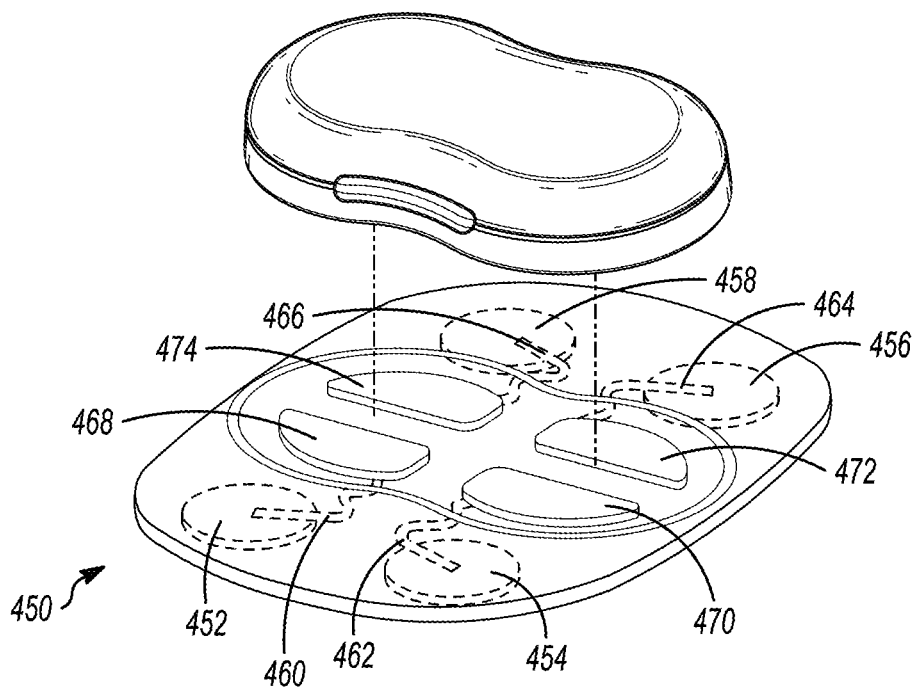
FIG. 4C is a partially-exploded perspective view of another illustrative medical device, in accordance with embodiments of the subject matter disclosed herein.
Figure 4D:
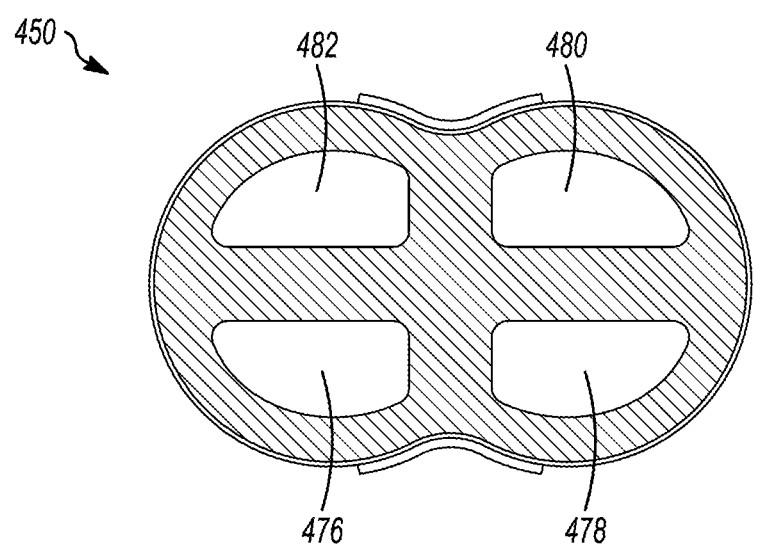
FIG. 4D is a bottom view of a first portion of the illustrative medical device depicted in FIG. 4C, in accordance with embodiments of the subject matter disclosed herein.

As indicated above, embodiments include any number of different arrangements of sensor connections. FIGS. 4A and 4B depict an illustrative medical device 400 having an arrangement of four sensing elements 402, 404, 406, 408; corresponding flexible circuit elements 410, 412, 414, 416; corresponding sensor connections 418, 420, 422, 424, and corresponding connections 426, 428, 430, and 432. FIGS. 4C and 4D depict an illustrative medical device 450 having an arrangement of four sensing elements 452, 454, 456, 458; corresponding flexible circuit elements 460, 462, 464, 466; corresponding sensor connections 468, 470, 472, 474, and corresponding connections 476, 478, 480, and 482. The device 400 and/or 450 may be, be similar to, include, or be included in medical device 102 depicted in FIG. 1, additional device 106 depicted in FIG. 1, medical device 202 and/or additional device 204 depicted in FIG. 2, and/or medical device 300 depicted in FIGS. 3A-3F.

The illustrative medical devices 400 and 450 shown in FIGS. 4A-4D are not intended to suggest any limitation as to the scope of use or functionality of embodiments of the present disclosure. The illustrative medical devices 400 and 450 should not be interpreted as having any dependency or requirement related to any single component or combination of components illustrated therein. Additionally, various components depicted in FIGS. 4A-4D may be, in embodiments, integrated with various ones of the other components depicted therein (and/or components not illustrated), all of which are considered to be within the ambit of the subject matter disclosed herein.

Various modifications and additions can be made to the exemplary embodiments discussed without departing from the scope of the presently disclosed subject matter. For example, while the embodiments described above refer to particular features, the scope of this disclosure also includes embodiments having different combinations of features and embodiments that do not include all of the described features. Accordingly, the scope of the subject matter disclosed herein is intended to embrace all such alternatives, modifications, and variations as fall within the scope of the claims, together with all equivalents thereof.

We claim:

1. A medical device configured to be adhesively coupled to an external surface of a subject, and configured to facilitate physiological monitoring of the subject, the device comprising:
    a first portion having a housing that at least partially encloses an interior chamber, the housing comprising an outside surface, the outside surface comprising:
        a lower outside surface comprising a first interface region, a first sensor connection, and a second sensor connection; and
    a second portion comprising a flexible patch configured to facilitate operably coupling the first portion to the subject, the flexible patch comprising:
        an upper surface comprising a third sensor connection and a fourth sensor connection, the upper surface including a second interface region corresponding to the first interface region, wherein the third sensor connection is configured to operably interface with the first sensor connection, and wherein the fourth sensor connection is configured to operably interface with the second sensor connection;
        a lower surface comprising a first sensing element and a second sensing element; and
        a flexible circuit assembly disposed between the upper and lower surfaces of the second portion, the flexible circuit assembly configured to electrically couple the third sensor connection to the first sensing element and the fourth sensor connection to the second sensing element so that, when the first portion is coupled to the second portion, the first and second sensor connection are operably coupled to the first and second sensing elements, respectively;
    an adhesive assembly configured to be disposed between the first portion and second portion to removeably couple the first portion to the second portion, the adhesive assembly comprising:
        a first conductive adhesive portion configured to be disposed between the third sensor connection and one of the first and second sensor connections;
        a second conductive adhesive portion configured to be disposed between the fourth sensor connection and the other one of the first and second sensor connections; and
        a non-conductive adhesive portion disposed around the first and second conductive adhesive portions; and
    an electronics module configured to be disposed within the interior chamber, wherein the electronics module is electrically coupled to the first and second sensor connections and is configured to receive electrical signals from the first and second sensor connections and determine, based on the received electrical signals, at least one physiological parameter measurement associated with the subject.

2. The medical device of claim 1, the flexible circuit assembly comprising:
    a first flexible element disposed between the upper and lower surfaces of the second portion, the first flexible circuit element extending between the third sensor connection and the first sensing element; and
    a second flexible circuit element disposed between the upper and lower surfaces of the second portion, the second flexible circuit element extending between the fourth sensor connection and the second sensing element.

3. The medical device of claim 1, further comprising:
    a third sensing element, a fourth sensing element, a fifth sensor connection, a sixth sensor connection, a seventh sensor connection, and an eighth sensor connection; wherein the lower surface of the second portion includes the third and fourth sensing elements, wherein the lower outside surface of the housing includes the fifth and sixth sensor connections, and wherein the upper surface of the second portion includes the seventh and eighth sensor connections;
    a third flexible circuit element disposed between the upper and lower surfaces of the second portion, the third flexible circuit element extending between the seventh sensor connection and the third sensing element; and
    a fourth flexible circuit element disposed between the upper and lower surfaces of the second portion, the fourth flexible circuit element extending between the eighth sensor connection and the fourth sensing element,
    wherein the fifth sensor connection is configured to operably interface with the seventh sensor connection, and wherein the sixth sensor connection is configured to operably interface with the eighth sensor connection so that, when the first portion is coupled to the second portion, the fifth sensor connection is operably coupled to the third sensing element and the sixth sensor connection is operably coupled to the fourth sensing element.

4. The medical device of claim 1, further comprising an alignment feature disposed on the upper surface of the second portion, the alignment feature comprising an indication of a border of the second interface region.

5. The medical device of claim 1, further comprising a disposable cover configured to be removeably disposed over at least a portion of the medical device.

6. The medical device of claim 1, the electronics module comprising a support structure disposed within the interior chamber, the support structure configured to receive and support an electronics assembly, wherein the support structure comprises an additional alignment feature configured to facilitate accurate alignment of the electronics assembly within the support structure.

7. The medical device of claim 1, wherein the second portion further comprises at least one sensor port, the at least one sensor port comprising an aperture disposed through at least a portion of the second portion and configured to facilitate exposure of a sensor to the subject, wherein the sensor comprises at least one of a chemical sensor, an acoustic sensor, an optical sensor, and a temperature sensor.

8. The medical device of claim 1, further comprising a grip portion comprising a first end section, a second end section, and a middle section disposed between the first end section and the second end section, wherein the grip portion has a peanut-like shape, wherein the first and second end sections are wider than the middle section.

9. The medical device of claim 8, the grip portion further comprising a plurality of grip structures disposed thereon to facilitate gripping.

10. A medical device configured to be adhesively coupled to an external surface of a subject, and configured to facilitate physiological monitoring of the subject, the device comprising:
- a first portion having a housing that at least partially encloses an interior chamber, the housing comprising a lower outside surface comprising a first interface region, a first sensor connection, and a second sensor connection;
- a second portion comprising a flexible patch configured to facilitate operably coupling the first portion to the subject, the flexible patch comprising:
  - an upper surface comprising a third sensor connection and a fourth sensor connection, the upper surface including a second interface region corresponding to the first interface region, wherein the third sensor connection is configured to operably interface with the first sensor connection, and wherein the fourth sensor connection is configured to operably interface with the second sensor connection;
  - a lower surface comprising a first sensing element and a second sensing element;
  - a first flexible circuit element disposed between the upper and lower surfaces of the second portion, the first flexible circuit element extending between the third sensor connection and the first sensing element so that, when the first portion is coupled to the second portion, the first sensor connection is operably coupled to the first sensing element; and
  - a second flexible circuit element disposed between the upper and lower surfaces of the second portion, the second flexible circuit element extending between the fourth sensor connection and the second sensing element so that, when the first portion is coupled to the second portion, the second sensor connection is operably coupled to the second sensing element;
- an adhesive assembly configured to be disposed between the first portion and second portion to removeably couple the first portion to the second portion, the adhesive assembly comprising:
  - a first conductive adhesive portion configured to be disposed between the third sensor connection and one of the first and second sensor connections;
  - a second conductive adhesive portion configured to be disposed between the fourth sensor connection and the other one of the first and second sensor connections; and
  - a non-conductive adhesive portion disposed around the conductive adhesive portions;
- an electronics module configured to be disposed within the interior chamber, wherein the electronics module is electrically coupled to the first and second sensor connections and is configured to receive electrical signals from the first and second sensor connections and determine, based on the received electrical signals, at least one physiological parameter measurement associated with the subject.

11. The medical device of claim 10, the housing of the first portion having an outside surface, the outside surface of the housing comprising a grip portion, the grip portion comprising:
- a peanut-like shape having a first end section, a second end section, and a middle section disposed between the first end section and the second end section, wherein the first and second end sections are wider than the middle section, and wherein the housing is designed such that a plane tangent to the grip portion at any one of a plurality of locations is oriented approximately perpendicularly to a plane corresponding to the lower outside surface of the lower housing; and
- a plurality of grip structures disposed thereon to facilitate gripping.

12. The medical device of claim 10, further comprising:
- a third sensing element, a fourth sensing element, a fifth sensor connection, a sixth sensor connection, a seventh sensor connection, and an eighth sensor connection; wherein the lower surface of the second portion includes the third and fourth sensing elements, wherein the lower outside surface of the housing includes the fifth and sixth sensor connections, and wherein the upper surface of the second portion includes the seventh and eighth sensor connections;
- a third flexible circuit element disposed between the upper and lower surfaces of the second portion, the third flexible circuit element extending between the seventh sensor connection and the third sensing element; and
- a fourth flexible circuit element disposed between the upper and lower surfaces of the second portion, the fourth flexible circuit element extending between the eighth sensor connection and the fourth sensing element,
wherein the fifth sensor connection is configured to operably interface with the seventh sensor connection, and wherein the sixth sensor connection is configured to operably interface with the eighth sensor connection so that, when the first portion is coupled to the second portion, the fifth sensor connection is operably coupled to the third sensing element and the sixth sensor is operably coupled to the fourth sensing element.

13. The medical device of claim 10, further comprising an alignment feature disposed on the upper surface of the second portion, the alignment feature comprising an indication of a border of the second interface region.

14. The medical device of claim 10, further comprising a disposable cover configured to be removeably disposed over at least a portion of the medical device.

15. The medical device of claim 10, the electronics module comprising a support structure disposed within the interior chamber, the support structure configured to receive and support an electronics assembly, wherein the support structure comprises an additional alignment feature configured to facilitate accurate alignment of the electronics assembly within the support structure.

16. A medical device configured to be adhesively coupled to an external surface of a subject, and configured to facilitate physiological monitoring of the subject, the device comprising:
   a first portion having a housing that at least partially encloses an interior chamber, the housing comprising an outside surface, the outside surface comprising:
      a lower outside surface comprising a first interface region, a first sensor connection, and a second sensor connection; and
   an electronics module configured to be disposed within the interior chamber, wherein the electronics module is electrically coupled to the first and second sensor connections and is configured to receive electrical signals from the first and second sensor connections and determine, based on the received electrical signals, at least one physiological parameter measurement associated with the subject;
   wherein the first portion is configured to be removeably coupled to a second portion via an adhesive assembly disposed between the first portion and the second portion, the second portion comprising a flexible patch configured to facilitate operably coupling the first portion to the subject, the flexible patch comprising:
      an upper surface comprising a third sensor connection and a fourth sensor connection, the upper surface including a second interface region corresponding to the first interface region, wherein the third sensor connection is configured to operably interface with the first sensor connection, and wherein the fourth sensor connection is configured to operably interface with the second sensor connection;
      a lower surface comprising a first sensing element and a second sensing element; and
      a flexible circuit assembly disposed between the upper and lower surfaces of the second portion, the flexible circuit assembly configured to electrically couple the third sensor connection to the first sensing element and the fourth sensor connection to the second sensing element so that, when the first portion is coupled to the second portion, the first and second sensor connection are operably coupled to the first and second sensing elements, respectively; and
   the adhesive assembly comprising:
      a first conductive adhesive portion configured to be disposed between the third sensor connection and one of the first and second sensor connections;
      a second conductive adhesive portion configured to be disposed between the fourth sensor connection and the other one of the first and second senor connections; and
      a non-conductive adhesive portion disposed around the first and second conductive adhesive portions.

17. The medical device of claim 16, wherein the second portion further comprises at least one sensor port, the at least one sensor port comprising an aperture disposed through at least a portion of the second portion and configured to facilitate exposure of a sensor to the subject, wherein the sensor comprises at least one of a chemical sensor, an acoustic sensor, an optical sensor, and a temperature sensor.

18. The medical device of claim 17, the sensor comprising a chemical sensor, the chemical sensor comprising a reagent disposed within the sensor port and a reaction-detection mechanism disposed in the first portion of the medical device.

19. The medical device of claim 16, further comprising an alignment feature disposed on the upper surface of the second portion.

20. The medical device of claim 16, further comprising a grip portion comprising a first end section, a second end section, and a middle section disposed between the first end section and the second end section, wherein the grip portion has a peanut-like shape, wherein the first and second end sections are wider than the middle section.

* * * * *